US012569242B2

(12) United States Patent
Mayer et al.

(10) Patent No.: US 12,569,242 B2
(45) Date of Patent: *Mar. 10, 2026

(54) DEVICE AND METHOD FOR FIXATING A SUTURE ANCHOR IN HARD TISSUE

(71) Applicant: SportWelding GmbH, Schlieren (CH)

(72) Inventors: Jörg Mayer, Niederlenz (CH); Mario Lehmann, Les Pommerats (CH); Stephanie Goebel-Mehl, Mettmenstetten (CH); Andreas Wenger, Muri b. Bern (CH)

(73) Assignee: SPORTWELDING GMBH, Schlieren (CH)

( * ) Notice: Subject to any disclaimer, the term of this patent is extended or adjusted under 35 U.S.C. 154(b) by 68 days.

This patent is subject to a terminal disclaimer.

(21) Appl. No.: 18/653,002

(22) Filed: May 2, 2024

(65) Prior Publication Data

US 2024/0277330 A1 Aug. 22, 2024

Related U.S. Application Data

(62) Division of application No. 17/243,811, filed on Apr. 29, 2021, now Pat. No. 11,974,737, which is a
(Continued)

(51) Int. Cl.
*A61B 17/04* (2006.01)
*A61B 17/00* (2006.01)
(52) U.S. Cl.
CPC .................... *A61B 17/0401* (2013.01); *A61B 2017/00831* (2013.01); *A61B 2017/00955* (2013.01);
(Continued)

(58) Field of Classification Search
None
See application file for complete search history.

(56) References Cited

U.S. PATENT DOCUMENTS 5,100,417 A * 3/1992 Cerier ................ A61B 17/0401
606/232
5,464,427 A 11/1995 Curtis et al.
(Continued)

FOREIGN PATENT DOCUMENTS

DE 112011102287 5/2013
EP 2221014 8/2010
(Continued)

*Primary Examiner* — Shaun L David
(74) *Attorney, Agent, or Firm* — Rankin, Hill & Clark LLP

(57) ABSTRACT

A device for fixating a suture anchor beyond a hard tissue opening with the aid of a material having thermoplastic properties and energy transmitted to the suture anchor for in situ liquefaction of at least part of the material having thermoplastic properties. The device includes a tool and a suture anchor. The tool has a proximal end suitable for being coupled to an energy source and a distal end suitable for arrangement of the suture anchor including the suture. The distal end includes a distal tool face and an axial channel with a distal mouth located in the distal tool face. The suture anchor has an anchor foot and a thermoplastic sleeve including the material having thermoplastic properties. The anchor foot holds a loop of a suture such that end sections of the suture reach through the thermoplastic sleeve and a portion of the distal tool face.

19 Claims, 7 Drawing Sheets

Related U.S. Application Data division of application No. 15/353,087, filed on Nov. 16, 2016, now Pat. No. 11,006,943, which is a division of application No. 14/018,599, filed on Sep. 5, 2013, now Pat. No. 9,526,490, which is a division of application No. 13/239,623, filed on Sep. 22, 2011, now Pat. No. 8,545,536.

(60) Provisional application No. 61/437,227, filed on Jan. 28, 2011, provisional application No. 61/386,160, filed on Sep. 24, 2010.

(52) U.S. Cl.
CPC ................. *A61B 2017/0409* (2013.01); *A61B 2017/0414* (2013.01); *A61B 2017/0417* (2013.01); *A61B 2017/0419* (2013.01); *A61B 2017/042* (2013.01); *A61B 2017/0424* (2013.01); *A61B 2017/0446* (2013.01); *A61B 17/0469* (2013.01); *A61B 2017/0496* (2013.01)

(56) References Cited

U.S. PATENT DOCUMENTS

| | | | |
|---|---|---|---|
| 5,522,844 A | 6/1996 | Johnson | |
| 5,709,708 A | 1/1998 | Thal | |
| 5,718,717 A * | 2/1998 | Bonutti | A61B 17/0401 606/232 |
| 5,725,529 A | 3/1998 | Nicholson et al. | |
| 5,733,307 A | 3/1998 | Dinsdale | |
| 5,824,011 A * | 10/1998 | Stone | A61B 17/0401 606/232 |
| 5,891,168 A | 4/1999 | Thal | |
| 5,993,458 A * | 11/1999 | Vaitekunas | A61B 17/0401 606/104 |
| 6,024,758 A | 2/2000 | Thal | |
| 6,056,751 A | 5/2000 | Fenton, Jr. | |
| 6,214,031 B1 | 4/2001 | Schmieding et al. | |
| 6,319,270 B1 | 11/2001 | Grafton et al. | |
| 6,508,830 B2 | 1/2003 | Steiner | |
| 6,511,499 B2 | 1/2003 | Schmieding et al. | |
| 6,517,564 B1 | 2/2003 | Grafton et al. | |
| 6,544,281 B2 | 4/2003 | ElAttrache et al. | |
| 6,569,188 B2 | 5/2003 | Grafton et al. | |
| 6,620,185 B1 | 9/2003 | Harvie et al. | |
| 6,641,597 B2 | 11/2003 | Burkhart et al. | |
| 7,008,226 B2 | 3/2006 | Mayer et al. | |
| 7,172,420 B2 | 2/2007 | Huguenin et al. | |
| 7,211,088 B2 | 5/2007 | Grafton et al. | |
| 7,226,469 B2 | 6/2007 | Benavitz et al. | |
| 7,329,272 B2 | 2/2008 | Burkhart et al. | |
| 7,335,205 B2 | 2/2008 | Aeschlimann et al. | |
| 7,442,202 B2 | 10/2008 | Dreyfuss | |
| 7,491,217 B1 * | 2/2009 | Hendren | A61F 2/0811 606/232 |
| 7,678,134 B2 | 3/2010 | Schmieding et al. | |
| 7,695,495 B2 | 4/2010 | Dreyfuss | |
| 7,785,347 B2 | 8/2010 | Harvie et al. | |
| 2002/0161401 A1 * | 10/2002 | Steiner | A61B 17/0401 606/232 |
| 2003/0225438 A1 | 12/2003 | Bonutti et al. | |
| 2004/0030341 A1 | 2/2004 | Aeschlimann et al. | |
| 2004/0068267 A1 | 4/2004 | Harvie et al. | |
| 2005/0222575 A1 | 10/2005 | Ciccone et al. | |
| 2005/0222618 A1 | 10/2005 | Dreyfuss et al. | |
| 2005/0222619 A1 | 10/2005 | Dreyfuss et al. | |
| 2005/0245932 A1 | 11/2005 | Fanton et al. | |
| 2006/0105295 A1 | 5/2006 | Mayer et al. | |
| 2006/0106423 A1 | 5/2006 | Weisel et al. | |
| 2006/0161159 A1 | 7/2006 | Dreyfuss et al. | |
| 2006/0253119 A1 * | 11/2006 | Berberich | A61B 17/0401 606/232 |
| 2007/0060922 A1 | 3/2007 | Dreyfuss | |
| 2007/0073299 A1 | 3/2007 | Dreyfuss et al. | |
| 2007/0203498 A1 * | 8/2007 | Gerber | A61B 17/0401 606/328 |
| 2007/0288027 A1 | 12/2007 | Grafton et al. | |
| 2008/0109037 A1 * | 5/2008 | Steiner | A61B 17/0401 606/232 |
| 2008/0109038 A1 * | 5/2008 | Steiner | A61B 17/0401 606/232 |
| 2008/0109080 A1 | 5/2008 | Aeschlimann et al. | |
| 2008/0208253 A1 | 8/2008 | Dreyfuss et al. | |
| 2008/0262544 A1 | 10/2008 | Burkhart | |
| 2008/0306511 A1 * | 12/2008 | Cooper | A61B 17/0401 606/232 |
| 2009/0018560 A1 | 1/2009 | Mayer et al. | |
| 2009/0131947 A1 | 5/2009 | Aeschlimann et al. | |
| 2009/0138053 A1 | 5/2009 | Assell et al. | |
| 2009/0171394 A1 | 7/2009 | Abdou | |
| 2009/0187216 A1 | 7/2009 | Schmieding et al. | |
| 2009/0192546 A1 | 7/2009 | Schmieding et al. | |
| 2009/0204152 A1 | 8/2009 | Blain | |
| 2009/0264928 A1 | 10/2009 | Blain | |
| 2010/0004683 A1 * | 1/2010 | Hoof | A61B 17/0401 606/232 |
| 2010/0023057 A1 | 1/2010 | Aeschlimann et al. | |
| 2010/0217266 A1 | 8/2010 | Helevirta et al. | |
| 2010/0262186 A1 | 10/2010 | Sodeika et al. | |
| 2011/0046670 A1 | 2/2011 | Lehmann et al. | |
| 2011/0112576 A1 | 5/2011 | Nguyen | |
| 2011/0118744 A1 | 5/2011 | Lehmann et al. | |
| 2011/0257694 A1 | 10/2011 | Mayer et al. | |
| 2012/0053622 A1 * | 3/2012 | Schulman | A61B 17/0401 606/232 |
| 2012/0179200 A1 | 7/2012 | Caldwell | |
| 2012/0191142 A1 | 7/2012 | Bouduban | |
| 2012/0239085 A1 | 9/2012 | Schlotterback | |
| 2012/0245631 A1 | 9/2012 | Lunn | |
| 2012/0245634 A1 | 9/2012 | Kaplan | |
| 2012/0330327 A1 | 12/2012 | McClellan | |
| 2013/0006276 A1 | 1/2013 | Lantz | |
| 2013/0006302 A1 | 1/2013 | Paulk | |
| 2013/0023930 A1 | 1/2013 | Stone | |
| 2013/0035721 A1 | 2/2013 | Brunelle | |
| 2013/0046340 A1 | 2/2013 | Huxel | |
| 2013/0072976 A1 | 3/2013 | Van Der Burg | |
| 2013/0123845 A1 | 5/2013 | Paulk et al. | |
| 2013/0138123 A1 | 5/2013 | Stone et al. | |
| 2013/0138152 A1 | 5/2013 | Stone | |
| 2013/0144334 A1 | 6/2013 | Bouduban | |
| 2013/0144335 A1 | 6/2013 | Sandow | |
| 2013/0150885 A1 | 6/2013 | Dreyfuss | |
| 2013/0184748 A1 | 7/2013 | Sojka et al. | |

FOREIGN PATENT DOCUMENTS

| | | |
|---|---|---|
| EP | 2486856 | 8/2012 |
| EP | 2537470 | 12/2012 |
| EP | 2596764 | 5/2013 |
| RU | 2 264 182 | 11/2005 |
| WO | 2008/128367 | 10/2008 |
| WO | 2008/131884 | 11/2008 |
| WO | 2009/055952 | 5/2009 |
| WO | 2009/109057 | 9/2009 |
| WO | 2009/132472 | 11/2009 |
| WO | 2009/141252 | 11/2009 |
| WO | 2010/045751 | 4/2010 |
| WO | 2010/117982 | 10/2010 |
| WO | 2011/119684 | 9/2011 |
| WO | 2011/133233 | 10/2011 |
| WO | 2011/140486 | 11/2011 |
| WO | 2012/006161 | 1/2012 |
| WO | 2012/030754 | 3/2012 |
| WO | 2012/036889 | 3/2012 |
| WO | 2012/129388 | 9/2012 |

* cited by examiner

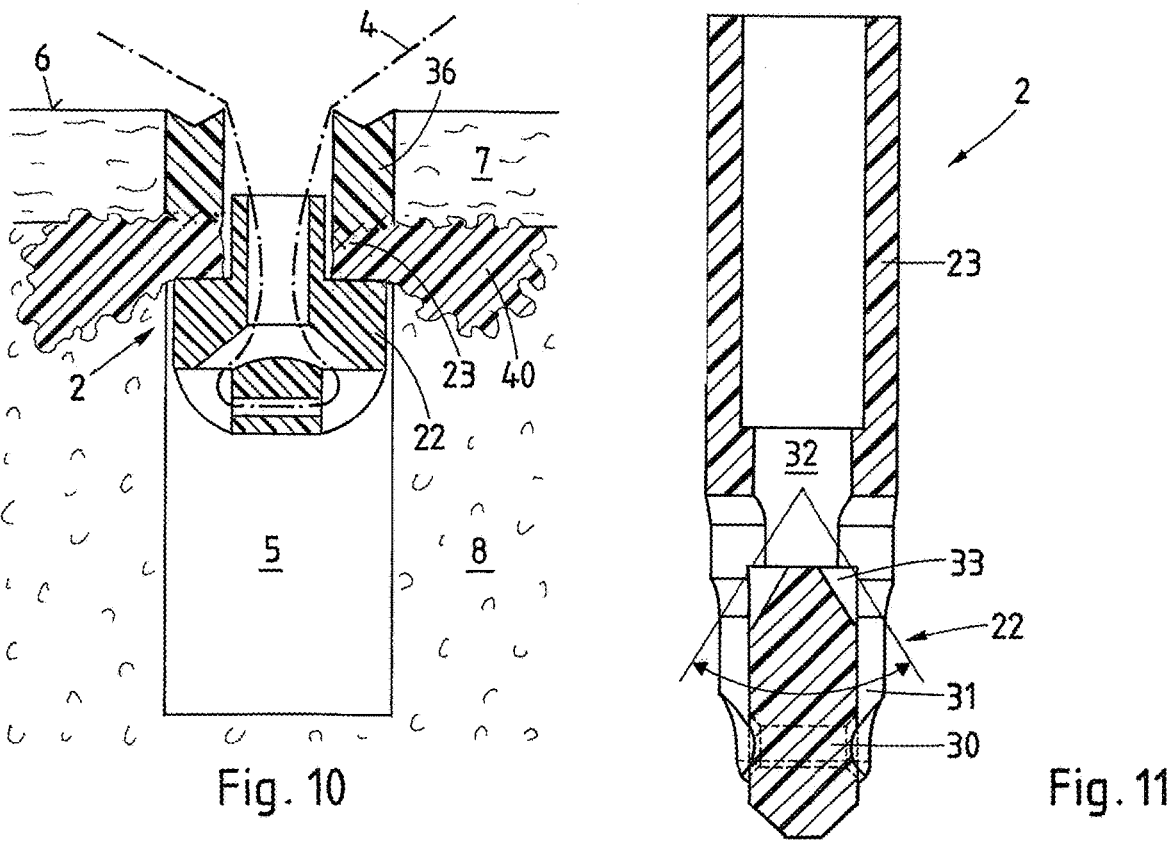
Fig. 10
Fig. 11
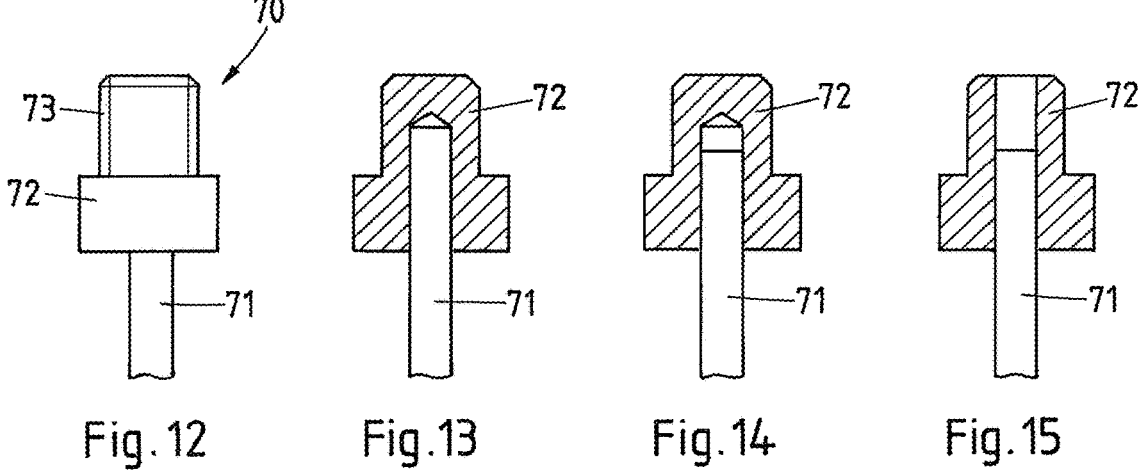
Fig. 12          Fig.13          Fig.14          Fig.15

DEVICE AND METHOD FOR FIXATING A SUTURE ANCHOR IN HARD TISSUE

FIELD OF THE INVENTION

The invention is in the field of medical technology and concerns a device and a method for fixating a suture anchor and therewith a suture in hard tissue in particular for attaching, with the aid of the suture, soft tissue to the hard tissue, wherein the hard tissue is in particular bone tissue of a human or animal patient. The invention also concerns an anchor applicable in the method according to the invention.

BACKGROUND OF THE INVENTION

The publication WO 2009/109057 (Woodwelding) discloses devices and methods for attaching a suture to hard tissue with the aid of a suture anchor, wherein the suture anchor comprises a material having thermoplastic properties and is anchored in a hard tissue opening with the aid of vibratory energy used for in situ liquefaction of the material having thermoplastic properties. The liquefied material penetrates into pores or other suitable structures of the hard tissue in the hard tissue opening, where on re-solidification it constitutes a positive fit connection between the hard tissue and the suture anchor. The devices as disclosed in the named publication comprise a vibration source in a housing, a vibration tool, a guide tube, the anchor, the suture and possibly a pushing bush. The proximal end of the vibration tool is coupled to the vibration source, the proximal end of the guide tube is supported on the housing, the anchor is arranged at the distal end of the vibration tool. The anchor comprises the material having thermoplastic properties in the form of a thermoplastic sleeve, the anchor or the vibration tool reaching through the sleeve and the sleeve being clamped between a foot piece of the anchor and the vibration tool, the guide tube or the pushing bush. A suture loop is held in the foot piece of the anchor, two suture end sections extending through further parts of the anchor and through portions of the vibrating tool and the guide tube from where they exit to possibly be kept straightened or tensioned by being attached to the guide tube or the housing.

For implantation, an opening is provided in the hard tissue and the distal end of the device or the suture anchor respectively is introduced into the opening, such that at least part of the thermoplastic sleeve is located in the opening, wherein a cross section of the opening is slightly larger than the cross section of the thermoplastic sleeve such that the material having thermoplastic properties is located near the hard tissue of the wall of the opening, but such that, on introducing the anchor into the opening, there is no friction between the sleeve and the wall of the opening. The vibration source is then activated and the material having thermoplastic properties of the thermoplastic sleeve being clamped between a vibrating element (vibration tool or anchor foot being coupled to the vibration tool) and a counter element (anchor foot not being coupled to the vibration tool, guide tube or pushing bush) is liquefied starting from its proximal and/or distal face and flows into the hard tissue, whereby the thermoplastic sleeve gets shorter. For maintaining the clamping force on the thermoplastic sleeve while the latter is getting shorter, device elements are moved relative to each other in an axial direction which is preferably effected by a pre-tensioned spring arranged together with at least the thermoplastic sleeve and the elements between which the thermoplastic sleeve is clamped in a closed load frame. This measure allows automatic anchoring of the suture anchor, the surgeon only having to position the device with the distal end of the guide tube on the surface of the hard tissue and to activate the vibration source. However, special measures are needed for allowing checking and tuning of the device before the anchoring process, without liquefaction of the material of the thermoplastic sleeve.

The publication US 2009/131947 (Woodwelding) also discloses a method for attaching a suture to hard tissue with the aid of a suture anchor comprising a thermoplastic material which is liquefied in situ with the aid of vibratory energy. The disclosed method is based on the same principle as the method which is briefly described above, wherein the suture is threaded through a distal end portion of the anchor, wherein a proximal end portion of the anchor comprises the thermoplastic material, and wherein a proximal face of the anchor is held against a distal face of a vibrating tool by pulling suture end portions in a proximal direction.

Further methods and devices for attaching sutures to hard tissue with the aid of suture anchors are disclosed in the publications U.S. Pat. Nos. 7,678,134, 7,695,495, US-2006/161159, US-2009/192546, US-2009/187216 (all to Arthrex), U.S. Pat. No. 5,733,307 (Dinsdale), or U.S. Pat. No. 6,508, 830 (Steiner), wherein the disclosed anchors comprise an interference screw to be screwed into a bone opening provided for the purpose or a plug preferably made of bone material and to be press-fitted into a bone opening provided for the purpose, wherein the suture is either held by the screw or plug or by an additional element being retained in the opening with the aid of the screw or plug.

Methods of anchoring an item in an opening provided in hard tissue, e.g. in bone tissue of a human or animal patient with the aid of a material having thermoplastic properties which is liquefied in situ and made to penetrate the hard tissue of the wall of the opening are disclosed in the publications U.S. Pat. Nos. 7,335,205, 7,008,226, US-2006/0105295, US-2008/109080, US-2009/131947, WO-2009/109057, and WO-2009/132472. The disclosure of all these publications and applications is enclosed herein by reference.

BRIEF SUMMARY OF THE INVENTION

Generally speaking, it is the object of the invention to create a further device and method for fixating a suture anchor and therewith a suture in hard tissue, wherein the suture fixated in the hard tissue with the aid of the suture anchor is to be in particular suitable for attaching soft tissue to the hard tissue, wherein the hard tissue is in particular bone tissue of a human or animal patient, and wherein one of the method steps comprises in situ liquefaction of a material having thermoplastic properties and bringing the liquefied material into contact with the hard tissue. The suture anchor is fixated in a hard tissue opening by penetration of the liquefied material into hard tissue walls of the opening or it is fixated beyond a hard tissue opening by the liquefied material expanding (flowing in radial direction) beyond the opening, i.e. on a non-accessible side of a hard tissue layer, possibly combined with penetrating the hard tissue surface on this non-accessible side of a hard tissue layer. On re-solidification the material which penetrated into the hard tissue constitutes a positive fit connection between this hard tissue and the anchor and/or the material expanded beyond the hard tissue opening constitutes a body which cannot pass the opening. The improvement achieved by the invention as compared with state of the art methods and devices serving the same purpose concern in particular the simplicity of method and device.

In particular, it is an object of the invention to create a further device and a further method for fixating a suture anchor in or beyond an opening in hard tissue of a human or animal patient, the suture anchor and the fixation being suitable in particular for the suture fixated with the aid of the suture anchor to be slideable relative to the anchor being fixated in the hard tissue. Therein, fixation of the suture anchor in the hard tissue, in particular underneath a cortical bone layer is to be effected with the aid of a material having thermoplastic properties and being liquefied in situ to be brought into contact with the hard tissue, in particular to penetrate into natural pores (trabecular structure) of the hard tissue or into suitable structures or cavities provided in the hard tissue, to preferably form, on re-solidification, a positive fit connection between the anchor and the hard tissue. The device and the method according to the invention are to constitute an improvement over the known state of the art, in particular regarding stability and simplicity of the device and simplicity of the whole fixation process including preparatory steps. Device and method according to the invention are to be suitable in particular for minimally invasive surgery but are to be applicable in open surgery also.

Device and method according to the invention constitute a further development of the devices and methods as disclosed in WO 2009/109057, the disclosure of which is included herein by reference in its entirety. Therein, the device is improved regarding stability against lateral forces acting on the anchor when arranged on a distal tool end and it is simplified by not needing a guide sleeve. Furthermore, it may comprise means for an easy mechanical and possibly visual control of the liquefaction of the material having thermoplastic properties. In addition, the device according to the invention may comprise a lever system which is operated by the surgeon and which facilitates handling of the suture, i.e. constitutes means for attaching, tensioning and moving the suture. The device according to the invention is easily operated by the surgeon with one hand, wherein he is able to operate the lever system with one finger of this hand. The lever system simplifies not only the implantation process but also the steps for preparing the device for the implantation process.

The device according to the invention comprises a tool with a proximal end suitable for being coupled to the energy source and a distal end suitable for arrangement of the suture anchor including the suture. In addition, the device comprises a substantially tube-shaped interface piece, which serves for stabilizing the anchor at the distal end of the tool, such that it can be safely positioned relative to the hard tissue and is kept aligned with the tool during the fixation procedure. The interface piece is designed to be displaceable in an axial channel of the distal tool end during the fixation procedure and to be removable from the fixation site together with the tool.

The device may further comprise an anchor including a suture, and possibly the energy source, the anchor being arranged at the distal end of the tool and the energy source being coupled to the proximal end of the tool. The energy source or a housing thereof may carry the above named lever system. The anchor comprises the material having thermoplastic properties in the form of a thermoplastic sleeve which is held between a distal tool face and an anchor foot and which, in the fixation process, is at least partly liquefied preferably starting from its proximal face in contact with the distal tool face, whereby the liquefied material flows away in a radial direction to penetrate hard tissue surrounding the liquefaction location or a cavity provided in this hard tissue, or to expand into soft tissue or a cavity beyond the hard tissue. For keeping the thermoplastic sleeve in close contact with the distal tool face during the liquefaction process the anchor foot is pulled relative to the tool in proximal direction with the aid of the suture, which is effected by the surgeon advantageously with the aid of the above named lever system.

The interface piece is dimensioned to reach through the thermoplastic sleeve, a distal end of the interface piece being couplable or coupled to the anchor foot and a proximal end reaching into an axial channel of the tool. During the liquefaction process the thermoplastic sleeve gets shorter and the anchor foot together with the interface piece are moved relative to the tool in a proximal direction. For mechanical control of the liquefaction process the tool may comprise a stop against which the proximal face of the interface piece abuts when the thermoplastic sleeve has reached a desired minimal axial length. For an additional visual control the tool may comprise a lateral recess or a see-through portion adjoining the stop distally, in which recess or see-through portion the movement of the proximal end of the interface piece can be visually controlled, during minimally invasive surgery through an arthroscope or during open surgery directly by the surgeon. For being removable together with the tool from the fixation site after completion of the fixation, the interface piece is caught in the axial channel of the tool at the latest on completion of the fixation process, such that it cannot be removed from the channel in a distal direction. The anchor foot is preferably connected with the interface piece with the aid of a push-on or clip-on connection which holds the two elements together when under no load, which stabilizes the two elements relative to each other under a compressive load, and which is de-connected easily under a small tensile load.

The suture runs in a loop through a system of channels and/or grooves in the anchor foot, the two end sections of the suture protruding from the proximal face thereof and running from there through the interface piece and the axial channel of the tool from where they exit preferably through the above named recess. The system of channels and/or grooves is preferably dimensioned such that the suture is easily slideable therethrough and such that, during implantation, the suture comes into contact neither with the hard tissue in the tissue opening nor with the liquefied material. This measure achieves that neither friction on the hard tissue nor thermal or mechanical influence of the liquefied or re-solidified material of the thermoplastic sleeve will impair the slideability of the suture through the implanted anchor. This does not only mean that after anchorage of the suture anchor the suture is held slideably by the latter but it also means that the suture may well be of a friction and/or heat sensitive type, consisting e.g. of a material having similar characteristics as the material of the thermoplastic sleeve.

For the fixation process, the tool is preferably supported on the hard tissue. For achieving liquefaction underneath a cortical bone layer or on a non-accessible side of a bone plate, the tool comprises a step at a distance from the distal tool face adapted to the thickness of the cortical bone layer or the bone plate. Therein the tool portion on the distal side of the step has a cross section smaller than the cross section of the opening and a tool portion on the proximal side of the step has a cross section larger than the cross section of the opening, such that the step limits introduction of the distal device end into the hard tissue opening by abutting against the hard tissue surface, when the interface between the distal tool face and the proximal face of the thermoplastic sleeve and therewith the liquefaction location is situated just below the cortical bone layer or on the other (non-accessible) side of the bone plate. During the liquefaction process, the tool is kept in the same position.

The energy source is preferably a vibration source, in particular a source of ultrasonic vibration (e.g. piezoelectric vibration generator possibly comprising a booster to which the tool is coupled) and the tool is suitable for transmission of the vibration from its proximal end to its distal face, preferably such that the distal face vibrates with a maximal longitudinal amplitude. For the in situ liquefaction the proximal face of the thermoplastic sleeve is held against the vibrating distal tool face, such creating friction heat at the interface. It is possible also to activate the tool to vibrate in a radial or in a rotational direction.

Alternatively, the energy source may be a laser, preferably emitting laser light in the visible or infrared frequency range and the tool is equipped for transmitting this light to its distal end, preferably via glass fiber. For the in situ liquefaction the laser light is absorbed near the distal tool face or in the thermoplastic sleeve held against the distal tool face, wherein in the latter case the material of the thermoplastic sleeve may contain particles or substances effecting such absorption. Furthermore, the energy source may be a source of electric energy which e.g. heats an electric resistor in a distal tool portion or which causes eddy currents and therewith thermal energy near the distal tool face or in the thermoplastic sleeve.

Suitable in situ liquefaction of a material having thermoplastic properties with the aid of vibration energy combined with an acceptable thermal loading of the tissue and suitable mechanical properties of the positive fit connection to be produced is achievable by using materials with thermoplastic properties having an initial modulus of elasticity of at least 0.5 GPa and a melting temperature of up to about 350° C. in combination with vibration frequencies preferably in the range of between 2 and 200 kHz (preferably 15 to 40 kHz, or even more preferably between 20 and 30 kHz). The modulus of elasticity of at least 0.5 GPa is in particular necessary if the material having thermoplastic properties is to transmit the vibration or mechanical forces without loss of mechanical stiffness. If the material having thermoplastic properties is not to transmit the vibration but is to be liquefied where it is in direct contact with the vibrating tool or if the material having thermoplastic properties is to transmit the vibration or mechanical forces, but is supported and guided by device parts of other materials, the material having thermoplastic properties may have a considerably smaller modulus of elasticity.

Materials having thermoplastic properties suitable for the thermoplastic sleeve of the device and the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (P E, Hostalen Gur 812, Höchst A G), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored, not with the aid of vibration energy, but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April;

21(4):351-74), J A Juhasz et al. Biomaterials, 2004 March; 25(6):949-55. Particulate filler types include: coarse type: 5-20 μm (contents, preferentially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

Anchor portions other than the thermoplastic sleeve may consist of any suitable material (e.g. polymer, metal, ceramic, glass) which material may be bio-resorbable or not bio-resorbable and liquefiable or not liquefiable. Non-bioresorbable or non-biodegradable such materials may comprise surfaces equipped for furthering osseointegration (e.g. per se known surface structures or coatings) where in contact with the bone tissue, in particular if the material of the thermoplastic sleeve is bio-resorbable or bio-degradable and therefore the anchoring function needs to be gradually taken over by osseointegration. Good results have e.g. been achieved with anchor feet of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with thermoplastic sleeves of PLDLLA 70%/30% (70% L and 30% D/L), as available from Böhringer as LR706. The PDLLA 70%/30% filled with 30% of biphasic calciumphosphate and similar materials prove to be suitable also for the thermoplastic sleeve and therefore suitable for manufacturing bio-resorbable, one-piece anchors being made of one material only.

As the tool can be designed very slim and with an axial length of 200 mm or even longer, the device and method according to the invention are in particular suitable for minimally invasive surgery but are also applicable in open surgery. If the tool is a vibration tool, it preferably has a length corresponding to half of the vibration wavelength in the tool material (or a multiple thereof). This half of the vibration wavelength is e.g. in titanium grade 5 and at a vibration frequency of 20 KHz 126.5 mm.

Device and method according to the invention as far as above described are applicable for all surgical procedures in a human or animal patient, in which surgical procedure a suture needs to be attached to hard tissue, in particular attached to be at least primarily slideable relative to the implanted anchor, and in particular to bone tissue with a cortical bone layer wherein the fixation of the anchor is preferably achieved underneath the cortical bone layer (so called sub-cortical fixation) in cancellous bone situated underneath the cortical bone layer, on the inner side of the cortical bone layer, or in a cavity or soft tissue adjoining the cortical bone layer on its inner side. In the same manner, the device and the method according to the invention are applicable for attaching a suture to a replacement material having features comparable to the features of hard tissue, or to part hard tissue part replacement material, or to a further implant (e.g. endoprosthesis) wherein the implant needs to be suitably equipped, e.g. with undercut openings. An example of such an application is the fixation of a soft tissue end to a bone, e.g. fixation of a rotator cuff to underlying bone tissue (or a corresponding endoprosthesis), Achilles tendon repair, or fixation of another ligament or tendon end to bone tissue using the technique of the so called double row procedure. For this procedure sutures are slideably attached to the bone by a row of medial anchors, are passed through the soft tissue, tensioned and, crossing each other, are non-slideably fixed (locked) with the aid of a row of lateral anchors, this second row running substantially parallel to the row of medial anchors.

When using the above discussed device and method according to the invention for the slideable attachment of the sutures, i.e. for anchoring the medial anchors, with the aid of the material having thermoplastic properties and preferably vibration energy it is advantageous to use a similar technique for the non-slideable attachment or locking of the sutures, i.e. for anchoring the lateral anchors, also.

As described further below, it is possible also to use the device and the method according to the invention not only for slideable fixation of a suture relative to a hard tissue but also for non-slideable such fixation or locking of the suture relative to the hard tissue respectively.

BRIEF DESCRIPTION OF THE DRAWINGS

Device and method according to the invention are described in further detail in connection with the appended Figs., wherein:

FIG. 10 shows the fixated anchor as shown in FIG. 2 and further equipped with a securing sleeve preventing damage of the edge of the mouth of the hard tissue opening by the suture or of the suture by this edge;

FIG. 11 shows a preferred embodiment of a suture anchor applicable in the device and method according to the invention;

FIGS. 12 to 15 show the proximal end portion of a vibration tool which is e.g. applicable in the device and method according to the invention.

DETAILED DESCRIPTION OF THE INVENTION

Figure 1:
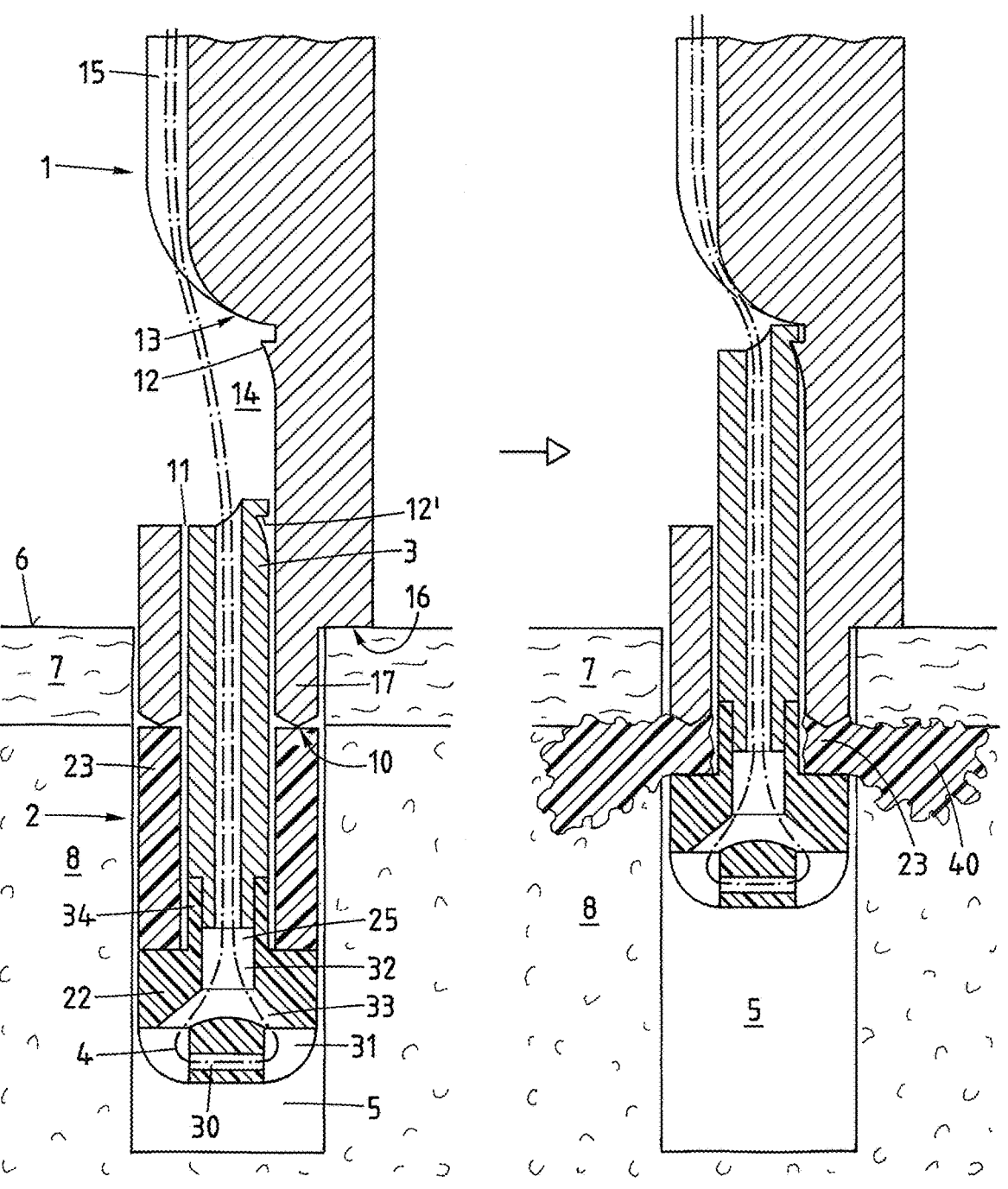
FIG. 1 illustrates an exemplary embodiment of the device according to the invention by showing a distal portion of the device before the anchoring procedure and after the anchoring procedure, this distal device portion comprising a distal portion of the tool, the interface piece, the suture anchor and the suture running through the anchor.

FIG. 1 shows a distal portion of an exemplary embodiment of the device according to the invention and illustrates in section the distal end of a tool 1, the suture anchor 2 and the interface piece 3. Also illustrated is the suture 4 (shown as dash-dotted line), which runs in a loop through the anchor 2, suture end sections extending through the interface piece 3 and through parts of the tool 1. The distal device portion is shown positioned relative to the hard tissue opening 5 before the liquefaction and anchoring process (left hand side of FIG. 1) and after this process (right hand side of FIG. 1), wherein the hard tissue opening 5 is e.g. an opening in bone tissue and reaches from a bone surface 6 through a cortical bone layer 7 into cancellous bone tissue 8.

The tool 1 comprises at its distal end a distal tool face 10 and extending axially from the distal tool face, an axial channel 11. The axial channel 11 comprises a first catch element 12, e.g. a wedge-shaped protrusion and in proximal direction following the first catch element 12 a stop 13 which ends the axial channel 11 or closes it at least partially. The stop 13 is constituted in the illustrated case by the proximal wall of a lateral recess 14, the recess opening the axial channel 11 laterally for visual inspection. The tool portion adjoining the lateral recess 14 in the proximal direction comprises a groove 15 aligned with the lateral recess 14 for accommodation of the suture 4. The tool 1 preferably further comprises an outer step 16, separating a distal end portion 17 of the tool 1 having a smaller cross section from a proximally adjoining portion having a larger cross section. As illustrated in FIG. 1, it is sufficient for the step 16 to extend only around part of the tool circumference. However it may also run around the whole tool circumference.

The suture anchor 2 comprises the anchor foot 22 and the thermoplastic sleeve 23, wherein the anchor foot 22 and the thermoplastic sleeve 23 may be separate items or wherein anchor foot 22 and thermoplastic sleeve 23 may constitute one piece. The anchor foot 22 comprises a system of channels and/or grooves 25 through which the suture 4 runs in a preferably slideable loop entering and exiting through the proximal face of the anchor foot 22. As illustrated in FIG. 1, the system of channels and/or grooves comprises e.g. a transversal first channel 30 extending substantially perpendicular to the anchor foot axis, and in the region of both mouths of this first channel 30 recesses 31 or grooves, as well as an axial second channel 32 extending to the proximal face of the anchor foot 22 and being connected to the recesses 31 or grooves through angled third channels 33.

For accommodation of more than one suture 4 the system of channels and/or grooves 25 may comprise more than one transversal first channels 30 being arranged axially spaced from each other and either parallel to each other or angled.

The interface piece 3 is substantially tube shaped and designed to extend loosely through the thermoplastic sleeve 23. The interface piece is coupled (or couplable) at a distal end to the anchor foot 22 and reaches beyond the proximal sleeve face when the distal sleeve face sits on the proximal face of the anchor foot 22. Coupling of the anchor foot 22 and the interface piece 3 is effected e.g. as illustrated between a tube-shaped anchor foot protrusion into which a distal end portion of the interface piece 3 is e.g. press-fitted. Instead of such press-fit coupling any per se known clip-on connection is applicable for which e.g. the distal end of the interface piece 3 comprises a ring-shaped ridge and the tube-shaped anchor foot protrusion comprises a ring-shaped groove adapted to the ridge. At its proximal end, the interface piece 3 comprises a second catch element 12', e.g. a depression, adapted to the first catch element 12 in the axial channel 11 of the tool 1 and cooperating with this first catch element 12 in a manner as described further below.

The suture anchor 2 is arranged at the distal end of the tool 1 with the proximal end of the interface piece 3 extending into the axial channel 11 of the tool 1 and the suture 4 extending from the proximal face of the anchor foot 22 through the interface piece 3 into the recess 14 of the tool 1 and from there into the groove 15. The thermoplastic sleeve 23 is kept between the distal face 10 of the tool 1 and the anchor foot 22 by the end sections or the suture 4 being held at a proximal end of the tool (see e.g. FIG. 4). The axial lengths of the interface piece 3, the thermoplastic sleeve 23 and the tool section adjoining the recess 14 in a distal direction are adapted to each other such that the proximal face of the interface piece 3 is just about visible in the recess 14, when the thermoplastic sleeve 23 has an initial maximum length. The stop 13 is distanced from the named position of the proximal face of the interface piece 3 by the length of the thermoplastic sleeve 23 which is to be liquefied. The catch elements 12 and 12' are arranged such that they catch each other before the proximal face of the interface piece 3 abuts the stop 13, the cooperating catch elements limiting distal movement of the interface piece 3 relative to the tool such that the interface piece cannot be removed from the channel 11, but possibly allowing further proximal movement.

In the case of the use of vibrational energy for the liquefaction process, it is advantageous to equip the distal face 10 of the tool 1 (or the proximal face of the thermoplastic sleeve 23) with energy directors, e.g. with an edge which limits contact with the thermoplastic sleeve to a line, and/or to rigidly attach the distal face of the thermoplastic sleeve 23 to the anchor foot 22, which is easily possible if the anchor foot 22 is made of a thermoplastic material, e.g. of PEEK to which the thermoplastic sleeve 23 can be welded. It is also possible to produce the anchor foot and thermoplastic sleeve as one piece consisting of the material having thermoplastic properties only (see also FIG. 11), e.g. of a polylactide polymer, e.g. PDLLA, preferably PDLLA 70%/30% filled with up to 30% of biphasic calciumphosphate. All the named measures help to ensure limitation of the liquefaction of the thermoplastic sleeve 23 to its proximal face. In an anchor foot made of a polymer prone to creep, it may be advantageous to strengthen the area most loaded by the suture tension, e.g. by lining the transverse suture channel 30 with a tube of a more resistant material such as e.g. a polylactide of a higher cristallinity or PEEK or by positioning a portion of such a material proximal to the transverse suture channel 30.

As it is most convenient to provide the hard tissue opening 5 for anchoring the suture anchor 2 by drilling, the anchor and at least the distal end portion 16 of the tool which is to be positioned in the opening 5 have advantageously a circular cross section. The same applies to the anchor foot 22, the interface piece 3 and the axial channel therethrough, as well as to the thermoplastic sleeve 23 and the axial channel 11 of the tool 1. However, this is not a condition for the invention, according to which any one of the named items may have a non-circular cross section. The only condition regarding cross sections is the condition for the thermoplastic sleeve 23 which is to fit into the opening 5 such that a sufficient part of the material to be liquefied is situated close to the wall of the opening 5. The cross section of the distal end portion 17 of the tool 1 and the cross section of the anchor foot 22 are preferably the same as the cross section of the thermoplastic sleeve 23 or they are slightly smaller than the latter.

For fixating the suture anchor 2 in the hard tissue opening 5 and therewith attaching the suture 4 relative to the hard tissue surface 6, the device according to the invention is positioned relative to the bone opening 5 as illustrated on the left hand side of FIG. 1. The energy source is coupled to the proximal end of the tool 1 (not shown), the interface piece 3 and the anchor 2 are arranged at the distal tool end with the suture 4 extending through the anchor foot 22, the interface piece 3, the axial channel 11 of the tool 1 and the recess 14 and is held further proximally to be at least straightened or slightly tensioned, such that the thermoplastic sleeve 23 is held between the proximal face 10 of the tool 1 and the anchor foot 22, and the tool 1 is positioned such that step 16 abuts against the bone surface 6. For starting liquefaction of the thermoplastic sleeve 23, the energy source is activated and possibly the suture tension increased. The liquefied material flows radially away from anchor 2 and tool 1 and the thermoplastic sleeve 23 gets shorter and is kept in contact with the distal face 10 of the tool 1 by pulling the suture 4 in a proximal direction and therewith pulling the anchor foot 22 nearer to the distal tool face 10, while the step 16 remains in contact with the bone surface 6.

The principle of the anchoring process is described (for different applications) e.g. in the publication US-2009/131947.

When working with a vibration tool and with a friction and/or heat sensitive suture it is particularly important not to tension the suture on activation of the energy source, but only when the proximal face of the thermoplastic sleeve is at least warmed such that it cannot transmit the vibration further distally or at least not fully. If the suture is tensioned at the moment of starting the vibration, it may happen that the vibrations are transmitted through the thermoplastic sleeve into the anchor foot which then vibrates relative to the suture. This may damage a sensitive suture before liquefaction of the thermoplastic sleeve starts. Further measures for preventing vibration transmission to the anchor foot are energy directors at the interface between the tool 1 and the thermoplastic sleeve as described further above and/or start of the vibration with a smaller starting amplitude which is increased after a starting interval in which the proximal end of the thermoplastic sleeve is warmed up.

With the liquefaction process advancing and the thermoplastic sleeve 23 getting shorter and the anchor foot 22 being pulled in a proximal direction, the interface piece 3 advances in the axial channel 11 of the recess 14 respectively, until the catch elements 12 and 12' come into catching interaction with each other and the proximal face of the interface piece abuts against the stop 13, which signifies the end of the liquefaction process as shown on the right hand side of FIG. 1. The advancement of the proximal end of the interface piece 3 and therewith the liquefaction process can be visually controlled in the recess 14.

At the end of the liquefaction process, the thermoplastic sleeve 23 has a minimal axial length and the liquefied and re-solidified material 40 of the thermoplastic sleeve 23 extends radially into the cancellous bone 8 and/or anchors the suture anchor 2 securely on the inside of the cortical bone layer 7. Furthermore, the interface piece 3 is caught in the axial channel 11 of the tool 1, which means on removing the tool 1 from the anchored suture anchor, the interface piece 3 is removed together with the tool 1.

For making sure that the suture 4 is not clamped between the proximal end of the interface piece 3 and the stop 13, when the proximal face of the interface piece abuts the stop 13, it is advantageous to design this proximal face and/or the stop 13 sloping, such that abutment of the interface piece 3 on the stop occurs only at the bottom of the recess 14, while the suture 4 is pulled away from this bottom, i.e. towards the opening of the recess 14. The named form of the proximal face of the interface piece 3 also results in an easier resiliency of the abutting portion of the proximal face of the interface piece 3 which can be made use of for the design of the second catch element 12'.

After completion of the liquefaction process, the suture 4 is released from being tensioned and held, and the tool 1 together with the interface piece 3 is removed from the opening 5 in which the suture anchor 2 is now safely anchored, and the suture is slideably attached to the bone tissue.

Figure 2:
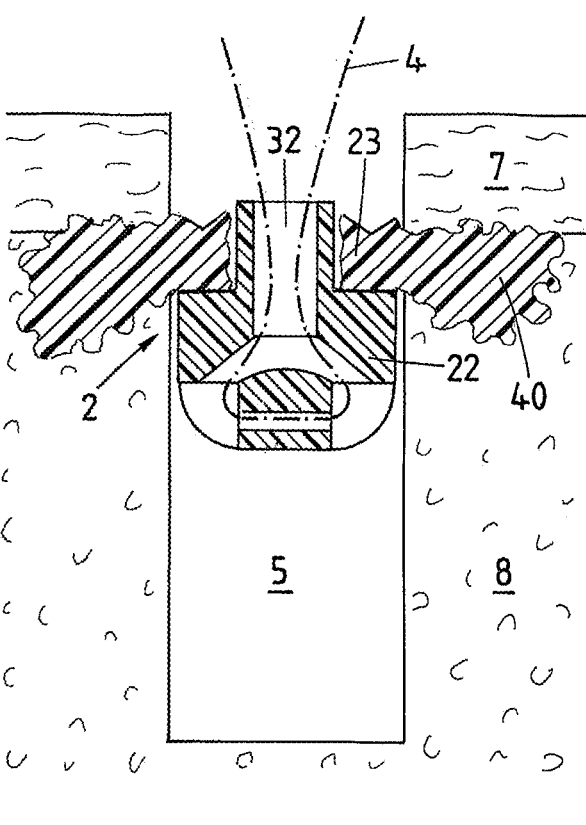
FIG. 2 shows the suture anchor as shown in FIG. 1 being fixated in the hard tissue opening.

FIG. 2 shows the result of the method as illustrated in FIG. 1, i.e. the suture 4 being attached to the hard tissue with the aid of the suture anchor 2 being anchored in the hard tissue opening 5 by the re-solidified material 40 situated in the hard tissue or bone tissue surrounding the opening, in particular in the cancellous bone tissue 8 just underneath the cortical bone layer 7 (subcortical fixation), the re-solidified material 40 being connected to remains of the thermoplastic sleeve 23. Obviously, the fixation process according to the invention is not dependent on the quality of the cancellous bone 8, which may even be completely absent. In the latter case the liquefied material may or may not penetrate the inner surface of the cortical bone layer and be held in the hard tissue opening mainly by the fact of constituting after re-solidification a body which cannot pass through the opening any more. This means that the fixation according to the invention is suitable not only for a subcortical fixation in cancellous bone of a reduced mechanical stability but also in absence of cancellous bone e.g. in the medullary cavity of long bones or on a non-accessible side of a bone plate.

Figure 3:
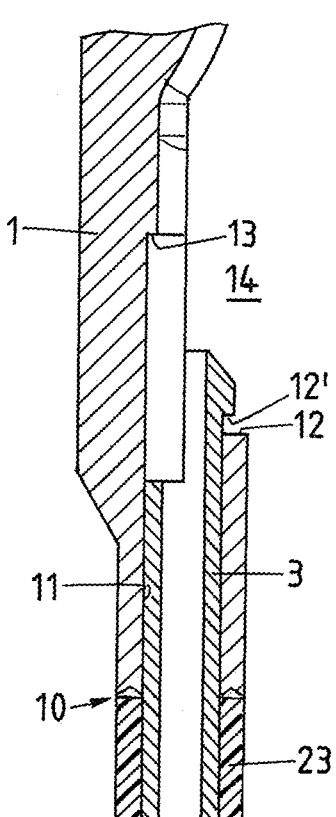
FIG. 3 shows a further exemplary embodiment of the distal tool portion and the interface piece of a device according to the invention.

FIG. 3 shows an alternative embodiment of the catch mechanism and the stop mechanism between the tool 1 and the interface piece 3 of a device according to the invention. The tool again comprises an axial channel 11 which extends at least through a distal tool portion and in which the substantially tubular interface piece 3 extends, and it comprises a recess 14 in which the proximal end of the interface piece 3 moves in a proximal direction during the liquefaction process. The first catch element 12 is constituted by the tool face at the distal side of the recess 14, the second catch element 12' is arranged on a proximal protrusion of the interface piece 3. The two catch elements keep the interface piece 3 caught in the axial channel 11 of the tool 1 even when the thermoplastic sleeve still has its original (maximum) length. This means that the interface piece which is removed from the tool for attaching the thermoplastic sleeve and the anchor foot to it, is caught in the axial tool channel 11 already on introducing the proximal end of the interface piece into the axial channel for preparing the device for the fixation procedure. During liquefaction of the material of the thermoplastic sleeve, the second catch element 12' is distanced in a proximal direction from the first catch element 12 and on removing tool 1 and interface piece 3 from the fixation site, the interface piece 3 is displaced into its most distal position, in which the two catch elements are in contact with each other.

The stop 13 of the tool according to FIG. 3 is arranged as step in the recess 14 and interacts with a portion of the proximal face of the interface piece 3 which portion is approximately opposite to the protrusion with the second catch element 12'. It is quite possible to not provide a stop 13 for the interface piece 3. In such a case, proximal movement of the interface piece 3 and the anchor foot will be ended at the last, when the thermoplastic sleeve 23 is fully liquefied and the anchor foot abuts against the distal tool face. It is further possible to limit the liquefaction process via the suture tension which can be effected e.g. with the aid of the lever system to be discussed in connection with FIG. 4.

Method and device according to the invention are suitable e.g. for establishing the medial anchors in the per se known double row procedure which is described further below in connection with FIG. 7 and which is used e.g. for rotator cuff repairs or Achilles tendon repairs. For this application, the suture is to be kept slideable relative to the anchor. Other exemplary applications of method and device according to the invention are e.g. regarding the human shoulder joint: the Bankart repair or the repair of SLAP-lesions (superior labrum anterior to posterior), regarding the human hand: the UCL-repair (ulnar collateral ligament), the SL-repair (scaphalunate ligament), the collateral ligaments repair, the flexor tendon reattachment, or the capsular reattachment of the metacarpophalangeal joint, and regarding the human foot: the Bromstrom ligament repair, treatment of the medial capsulorrhaphy hallus valgus, or the peroneal retinacular repair.

The distal end of the device according to the invention, which is shown in FIGS. 1 to 3 and the fixation method carried out which the aid of such a device may be varied e.g. in the following manner without departing from the basic idea of the invention:

Instead of the illustrated catch elements 12 and 12', any per se known pair of catch elements may be used, wherein it is advantageous to design the catch elements such that, at least during the fixation process, friction between the tool 1 and the interface piece 3 is kept as low as possible and/or is occurring only during a last portion of the advancement of the interface piece 3 in the axial channel 11 of the tool 1.

Instead of the lateral recess 14, the tool 1 may comprise a see-through portion which allows visual inspection of the movement of the proximal end of the interface piece 3 in the axial channel 11 of the tool 1 and the suture 4 extends to the outside of the tool through a separate opening or through a slot extending from the distal tool face at least to the stop 13.

The tool comprises no means for visual inspection.

The recess 14 is narrow but extending right to the distal tool face, the interface piece 3 comprising for visual control of the fixation process a flag extending into the recess and possibly protruding from the recess and being visible from the outside of the tool 1.

The axial position of the stop 13 is selectable by designing the stop as a separate stop element which can be fixed in the recess 14 in varying axial positions, or as a selection of separate stop elements of varying axial lengths which can be fixed in the recess 14.

Instead of the system 25 of channels and/or grooves which holds the suture 4 in a distal region of the anchor foot 22, the anchor foot comprises an eyelet protruding from its proximal face or other suitable proximal means for holding the suture 4 in a slideable manner.

The suture 4 is held in the anchor foot 22 in a non-slideable manner, e.g. with the aid of a knot or suture retainer being retained in a distal recess having a larger cross section than a proximally adjoining channel in which the suture extends in a proximal direction, or by a suture end or loop being molded into the anchor foot.

The tool 1 does not comprise a step 16 limiting the axial length of the distal tool portion 17 having a cross section adapted to fit into the hard tissue opening 5 or the step 16 has a further proximal position. This means that the distal tool end can be introduced into the hard tissue opening 5 to a depth which can be chosen by the surgeon, or the distal tool end can be introduced into the hard tissue opening to reach the bottom face of this opening when the fixation process is started. During the fixation process, the distal tool end can then be moved deeper and deeper into the hard tissue opening while the thermoplastic sleeve 23 gets shorter through liquefaction, the anchor foot 22 remaining positioned against the bottom face of the hard tissue opening 5. Other than above described in connection with FIG. 1, in such a case, during the liquefaction step it is not the tensioned suture which holds the thermoplastic sleeve 23 against the vibrating tool and it is not the bone surface 6 which supports the tool, but both these functions are taken over by the bottom face of the hard tissue opening. This means that the bone tissue of this bottom face needs to have a corresponding mechanical strength while the necessary mechanical strength of the suture needs to be adapted solely to the tissue attaching function of this suture.

The anchor foot 22 is adapted, by e.g. having a tapering or sharpened distal end, for being able to be forced at least into cancellous bone without the necessity of providing an opening therein beforehand or of providing such opening only through the cortical bone. The forcing of the anchor foot 22 into the bone tissue is effected by positioning the anchor foot 22 arranged at the distal tool end as shown in FIG. 1 and by applying a corresponding force to the tool 1, the force being transmitted to the anchor foot 22 via the thermoplastic sleeve 23. The liquefaction process is started by activation of the energy source (e.g. vibration source), only when the anchor foot 22 has reached a desired depth in the bone tissue. If the forcing of the anchor foot 22 into the bone tissue is to be supported with vibrational energy, transmission of the pressing force and the vibration from the tool 1 to the anchor foot 22 via the thermoplastic sleeve 23 is to be prevented for preventing undesired liquefaction of the thermoplastic sleeve 23 during the forcing step. This can be effected by transmitting force and vibration to the anchor foot via the interface piece 3 and by making sure that the thermoplastic sleeve 23 sits only loosely between the distal tool face and the anchor foot, e.g. by introducing into the recess 14, a block element which prevents proximal movement of the interface piece and is able to transmit vibration and force from the tool 1 to the interface piece. The block element is to be removed for the anchoring step.

The anchor foot 22 is equipped for being forced into the hard tissue (at least cancellous bone tissue) without providing an opening beforehand, e.g. by comprising a pointed or otherwise sharp distal end and it is forced into the hard tissue e.g. assisted by ultrasonic vibration, wherein for transmitting the necessary pushing force and the vibration to the anchor foot 22 the interface piece 3 or another suitable pushing tool is used. The thermoplastic sleeve is either fixed to the anchor foot or not. When the anchor foot has reached the desired depth and, if applicable, after removal of the pushing tool and mounting of the interface piece 3 on the anchor foot 22, and, if applicable after mounting the thermoplastic sleeve 23, the distal end of the tool 1 is positioned on the proximal face of the thermoplastic sleeve and the fixation step is carried out as described above in connection with FIG. 1. Instead of forcing the anchor foot into the hard tissue, it is possible also to screw it into the hard tissue, wherein the interface piece 3 or any other suitable tool can be used for transmitting the rotation to the screw-shaped anchor foot.

Figure 4:
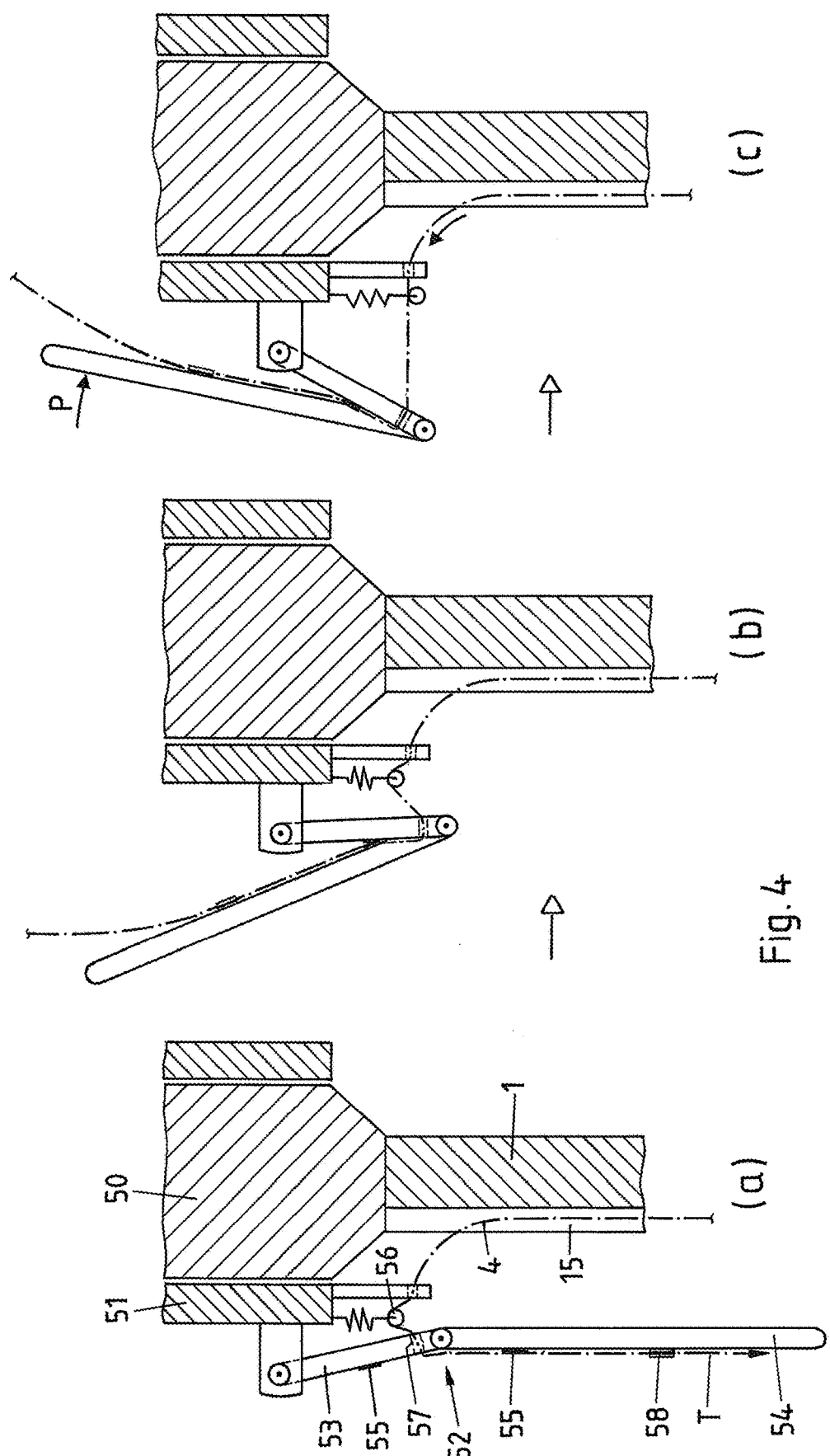
FIGS. 4 and 5 further illustrate an exemplary embodiment of the device according to the invention by showing an exemplary embodiment of the proximal portion of the device comprising a proximal portion of the tool, the energy source with the housing and, attached to the housing, the lever system for fastening and tensioning the suture and for moving the anchor foot with the aid of the suture.

FIG. 4 shows a proximal end portion of an exemplary embodiment of the device having a distal end as e.g. described above in connection with FIGS. 1 to 3. This proximal end portion is shown in axial section and comprises the proximal end of the tool 1 which is coupled to the energy source 50 (preferably ultrasonic vibration generator) arranged in a housing 51, and the two end sections of the suture 4 (dash dotted line). The proximal end portion of the device further comprises a lever system 52 serving as means for fastening and straightening and/or tensioning the suture 4 and for moving the anchor foot in a proximal direction relative to the tool 1 with the aid of the suture 4 extending through the anchor foot (as shown in FIG. 1). The lever system 52 is arranged preferably on the housing 51 of the energy source 50 but may possibly also be arranged on the energy source or on a proximal portion of the tool 1. The lever system 52 is designed for being operated by the surgeon.

In FIG. 4, the proximal device portion and in particular the named lever system 52 is illustrated in three configurations (a), (b) and (c) into which it is brought in succession for one anchoring process. Configuration (a) serves for introducing the end sections of the suture 4 into the lever system. In configuration (b) the end sections of the suture are fastened by being clamped or braked (through bending around at least one small radius) in the lever system and in configuration (c) the fastened end portions of the suture 4 are moved away in a radial and proximal direction from the tool 1 and the housing 51 thereby straightening or tensioning the suture and moving the anchor foot (see FIG. 1) relative to the tool as soon as liquefaction of the thermoplastic sleeve has started.

The exemplary embodiment of the lever system 52 as illustrated in FIG. 4 comprises a clamping arm 53 and a tensioning arm 54, the clamping arm 53 being arranged on the housing 51 in a pivoting manner, the tensioning arm 54 being connected in an articulating manner to the free end of the clamping arm 53, and the tensioning arm 54 being longer than the clamping arm 53 and advantageously equipped with an end section suitable for activating the system by hand (not shown). Each one of the arms 53 and 54 of the lever system 52 comprises means for fastening the suture between the two arms, e.g. a pair of clamping jaws 55 arranged for clamping the suture end sections between each other when the arms 53 and 54 are pivoted relative to each other to extend away from their articulating connection in substantially the same direction. The arms are further equipped for being locked to each other (e.g. snap connection) in this fastening position, wherein the connector function may be integrated in the clamping jaws 55.

FIG. 4 also shows the groove 15 which has already been discussed in connection with FIG. 1 and which preferably reaches right up to the proximal tool end and serves for accommodating the suture 4, wherein the groove 15 and the lever system 52 are aligned to each other. FIG. 4 further shows a suture guide 56 arranged between the groove 15 and the lever system 52.

Fastening the end sections of the suture 4 to the lever system, straightening or tensioning of the suture 4 and moving the anchor foot with the aid of the suture are achieved in the following manner: For threading the end sections of the suture 4 through the lever system 52, the two arms are brought into a substantially stretched-out position, advantageously stretched out in a distal direction (configuration (a)). The end sections of the suture 4 running along the groove 15 or, if no groove is provided, just along the tool 1 towards the proximal tool end are threaded through the suture guide 56 and an eyelet 57 reaching through one of the arms 53 and 54 to the one (outer) side of the arms, which, in this arm configuration, faces away from the tool 1. The suture ends are then threaded through a further eyelet 58 on this outer side of the tensioning arm 54 to extend, guided by the two eyelets 57 and 58, past the clamping jaw 55 of the tensioning arm 54. The end sections of the suture 4 are then held at the free end of the tensioning arm 54 to extend straightened-out but hardly tensioned along the described path (arrow T, configuration (a)). The tensioning arm 54 is then pivoted against the clamping arm 53 while the end sections of the suture 4 are still held at the free end of the tensioning arm 54 until the suture 4 is clamped between the clamping jaws 55 and the arms 53 and 54 are locked relative to each other in the clamping position (configuration (b)). In this configuration the device is checked and possibly tuned by shortly activating the energy source. After such checking and possible tuning, the device is ready for the implantation of the suture anchor.

During such implantation, the suture 4 is tensioned by pulling the free end of the tensioning arm 54 against the housing 51 thereby moving its other end, to which the suture end sections are fastened, away from the housing 51 and in a proximal direction, and the energy source 50 is activated to start liquefaction. During the liquefaction process, the pressure on the tensioning arm 54 (arrow P in configuration (c)) is maintained and the free end of the tensioning arm 54 moved closer to the housing 51 or its other end further away from the housing 51 and more proximally thereby moving the anchor foot in a proximal direction (configuration (c)).

The lever system 52 as shown in FIG. 4 may further comprise means for controlling the suture tension and the liquefaction process or the proximal movement of the anchor foot respectively. For guaranteeing a minimal suture tension or a straight suture extension when the suture is initially threaded and fastened in the lever system, a roller 59 may be attached to the housing 51 in a resilient manner (e.g. via a spring) to be positioned between the eyelets 56 and 57. If the suture is passed around the roller 59, the roller takes up slack in the suture by being driven away from the eyelets by the spring. On activation of the lever system for tensioning the suture, the roller 59 is moved into its most extended position aligned with the two eyelets. The resiliency of the fixation of the roller 59 can be achieved as illustrated with the aid of a tension spring but also with the aid of a pressure spring or any other per se known means (e.g. mechanical, pneumatic or hydraulic) for not only taking up suture slack and keeping suture tension approximately constant but also for absorbing vibration or shock which may damage the suture.

The lever system 52 can also take over the function of the stop as discussed in connection with FIGS. 1 and 3, in the simplest case by abutting the housing, when the anchor foot has reached its desired most proximal position. The liquefaction process and its desired end can also be controlled via the suture tension by designing a distal portion of the tensioning arm to be resilient and therefore to be capable of tensioning the suture with a desired maximum force only and on application of more force to just bend. This measure for controlling the liquefaction process not only allows the process to be stopped when the thermoplastic sleeve is exhausted but also when the capacity of the hard tissue to be penetrated by the liquefied material is exhausted and only a force of an undesired size could press more material into the tissue. This means that in the latter case the liquefaction process is controlled independent of the extension of the suture under tension, and in dependence of the hard tissue in which the anchor is to be fixated. Furthermore, limitation of the suture tension e.g. in the named way makes sure that the suture is not damaged during the fixation process.

Figure 5:
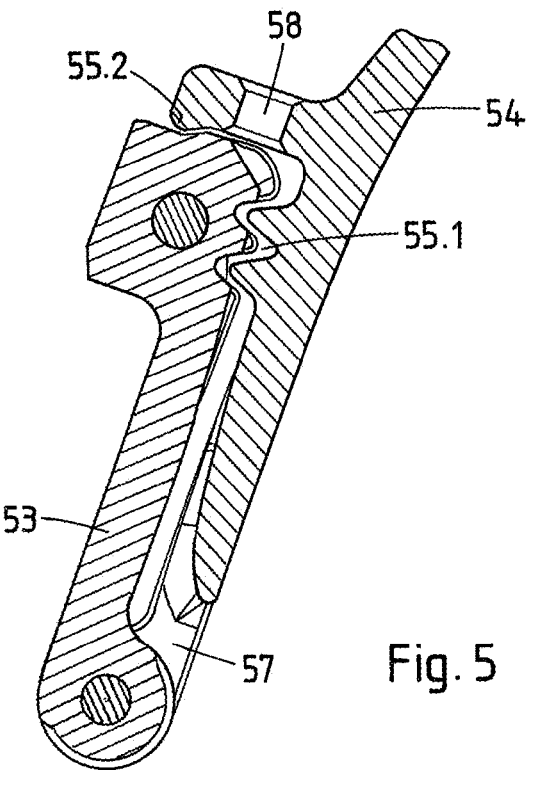

FIG. 5 illustrates a further exemplary embodiment of the means for fastening the suture in the lever system and the means for locking the clamping arm 53 and the tensioning arm 54 in the clamping position. Similar items are designated with same reference numerals as in FIG. 4. Instead of the clamping jaws 55 as shown in FIG. 4, the two arms comprise cooperating curved profiles 55.1 which loosely mesh when the two arms 53 and 54 are in the clamping position, wherein the curves of the curved profiles have a number large enough and/or a radius small enough for sufficiently braking a suture running between the two profiles for preventing suture movement through the gap between the profiles. The advantage of the fastening means according to FIG. 5 is the fact that the suture does not need to be clamped and therewith to be deformed regarding cross section, which may damage a sensitive type of suture.

The means for locking the clamping arm 53 and the tensioning arm 54 in the clamping position as shown in FIG. 5 is a snap connection 55.2 comprising a protrusion on the tensioning arm 54 and a corresponding depression on the clamping arm 53, wherein the protrusion is resilient enough for being snapped into the depression.

Instead of the above described lever system 52, the device may comprise a ratchet mechanism or just a pawl being biased against a surface of e.g. the housing 51 to clamp the suture end sections against this surface and being designed for allowing suture movement in only one direction, or it may comprise any other per se known mechanism which allows fastening and straightening or tensioning of the suture 4 and movement of the anchor foot with the aid of the suture while maintaining the suture tension, wherein the surgeon either operates the mechanism by pulling on the suture ends or the mechanism comprises a member to be handled by the surgeon. In a very simple embodiment of the device there may be no such means for attaching, tensioning and moving, wherein it is left to the surgeon to hold on to the suture and tension it and to therewith move the anchor foot.

Figure 6:
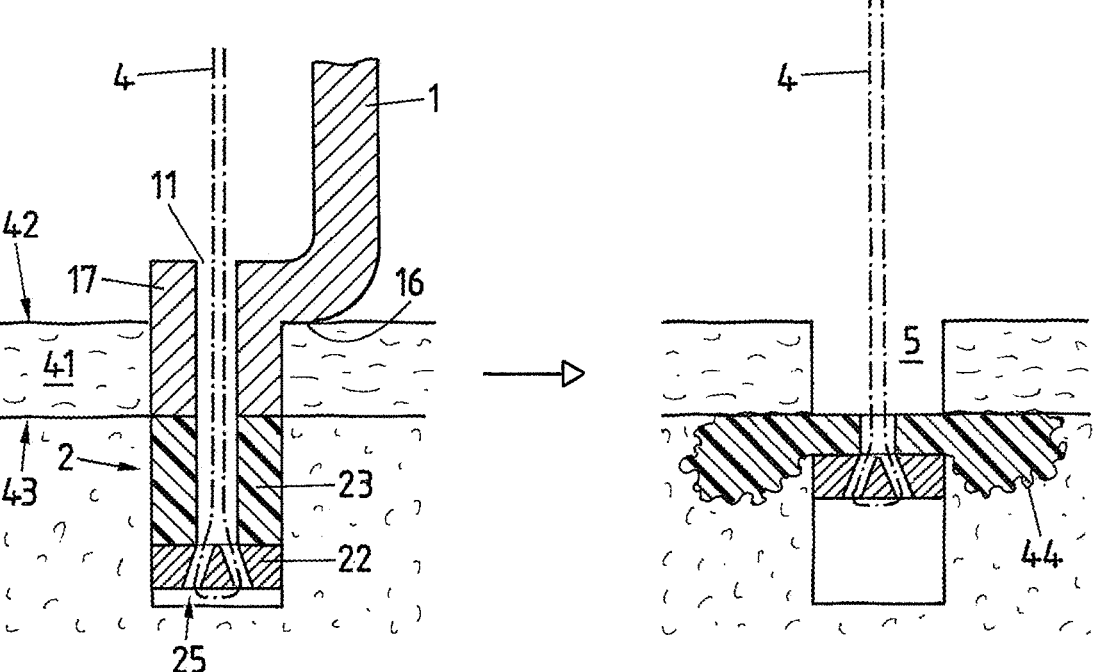
FIG. 6 illustrates a further exemplary embodiment of the method according to the invention and of the anchor being fixated with the aid of the method.

FIG. 6 illustrates the method as mentioned already further above which method serves for fixation of a suture anchor beyond a hard tissue opening, i.e. in a cavity or soft tissue on a non-accessible side of a hard tissue layer (e.g. in the medullary cavity of a long bone, in a location underneath a cortical bone layer where there is no cancellous bone tissue, or on the non-accessible side of a bone plate or a prosthesis replacing a bone plate). The device shown in FIG. 6 is a simplified version of the device as shown in FIGS. 1 and 3.

The opening provided for the fixation of the suture anchor 2 is a so called supra-cortical fixation in which the hard tissue opening provided for the fixation of the suture anchor does not reach into hard tissue (e.g. into cancellous bone tissue below a cortical bone layer) but reaches through a bone 41 from an accessible side 42 to a non-accessible side 43 thereof and wherein instead of a subcortical anchorage a supra-cortical button 44 is formed. This supra-cortical button 44 may or may not be anchored in the bone surface of the non-accessible bone side. The method according to which the fixation is established is quite similar to the one as described in connection with FIGS. 1 to 5.

In the simplified embodiment of the device, the suture anchor 2 again comprises an anchor foot 22 and a thermoplastic sleeve 23, a loop of the suture 4 being held preferably slideably in the anchor foot (system 25 of channels and/or grooves) and end sections of the suture reaching through the thermoplastic sleeve 23 and a distal portion 17 of the tool 1, which distal tool portion 17 again comprises an axial channel 11 and whose axial length is determined to be approximately equal to the thickness of the bone 41 by a corresponding position of a step 16. In particular, when using a relatively short thermoplastic sleeve 23 it is possible to not use the interface piece as shown in FIGS. 1 and 3. By either fixing the distal face of the thermoplastic sleeve 23 to the anchor foot 22 or by providing energy directors at the distal face 10 of the tool 1 or at the proximal face of the thermoplastic sleeve 23, preferable liquefaction of the thermoplastic sleeve at its proximal end is provoked.

If the suture 4 is to still be slideably held by the anchor foot 22 and the supra-cortical button 44 after the fixation process, it is preferable to equip the anchor foot 22 with a tube-shaped proximal protrusion (not shown) reaching into the cannulation of the thermoplastic sleeve 23 and having an axial length at least as great as the final thickness of the supra-cortical button 44 and/or to use an interface piece as shown in FIGS. 1 and 3. If slideability of the suture is not important, the anchor foot 22 can be flat as illustrated, and the interface piece can be omitted. Therewith the suture may or may not be locked by the liquefied material of the thermoplastic sleeve 23.

Obviously, for the method as shown in FIG. 6, there is no need for the cross section of the thermoplastic sleeve 23 to be adapted to the cross section of the hard tissue opening 5 such that the sleeve material is situated in close proximity to the wall of the opening as discussed in connection with FIGS. 1 and 2. It is required that anchor foot 22, thermoplastic sleeve 23 and preferably the distal end of the tool 1 fit into and trough the opening 5 and that there is enough sleeve material for producing a body 44 which cannot pass through the opening 5

Exemplary applications of supra-cortical buttons 44 established as above described are e.g. regarding the human shoulder: acute acromioclavicular joint stabilization; and regarding the human foot: fixation of syndesmosis disruptions. In the named applications, the suture 4 fixated by the supra-cortical button may be a suture bundle which is used to directly replace a tendon or ligament.

Figures 7, 8:
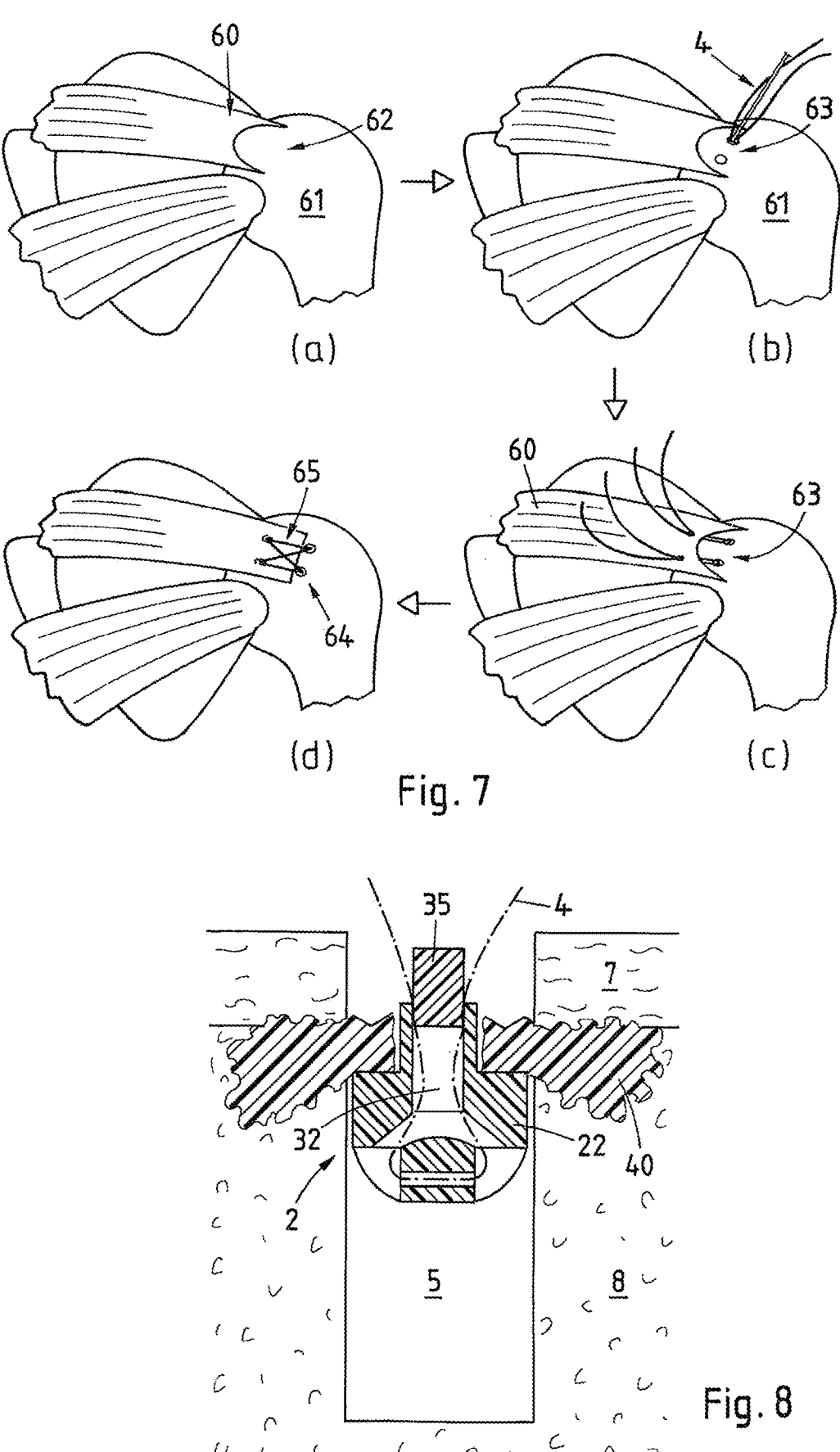
FIG. 7 illustrates four successive phases of the per se known double row procedure using the example of a rotator cuff repair.
FIG. 8 shows the fixated anchor as shown in FIG. 2 and further equipped with a locking plug for locking the suture relative to the anchor.

FIG. 7 illustrates the per se known double row procedure for suturing a soft tissue to a hard tissue, using the example of reattaching a torn rotator cuff tendon 60 to humeral bone tissue 61 (or a corresponding endoprosthesis) in four successive phases (a), (b), (c) and (d). Phase (a) is before the repair operation and shows the location 62 in which reattachment is necessary. In phase (b) two medial anchors 63 are fixated in the bone tissue, in locations to eventually be located underneath the tendon 60, each one of the medial anchors 63 attaching at least one suture 4 to the bone tissue in a slideable manner. In phase (c), the end sections of each suture attached to one of the medial anchors is passed through the torn tendon 60 and by tensioning the sutures away from the tendon end (not shown), the latter is pulled over the medial anchors 63. In phase (d) two lateral anchors 64 are anchored in the bone tissue just beyond the edge of the tear, the row of lateral anchors 64 running about parallel to the row of medial anchors 63, the end sections of the sutures 4 being tensioned and locked with the aid of the lateral anchors 64 in a cross-wise manner, such that the two suture end sections held by one medial anchor 63 are locked by two different lateral anchors 64, such forming crossed suture bridges 65 between the row of medial anchors 63 and the row of lateral anchors 64.

If in a double row procedure in which for establishing the medial anchors 63 methods and devices according to the invention are used it is advantageous to establish the lateral anchor row using also a fastening technique based on in situ liquefaction of a material having thermoplastic properties or even similar anchors as described above and being further equipped for suture locking (see FIGS. 8 and 9), wherein each row of anchors may comprise two or more than two anchors and wherein each medial anchor 63 is used for attaching at least one suture 4 (two suture end portions) and each lateral anchor 64 is used for locking at least two suture end portions originating from two different medial anchors 63.

Figure 9:
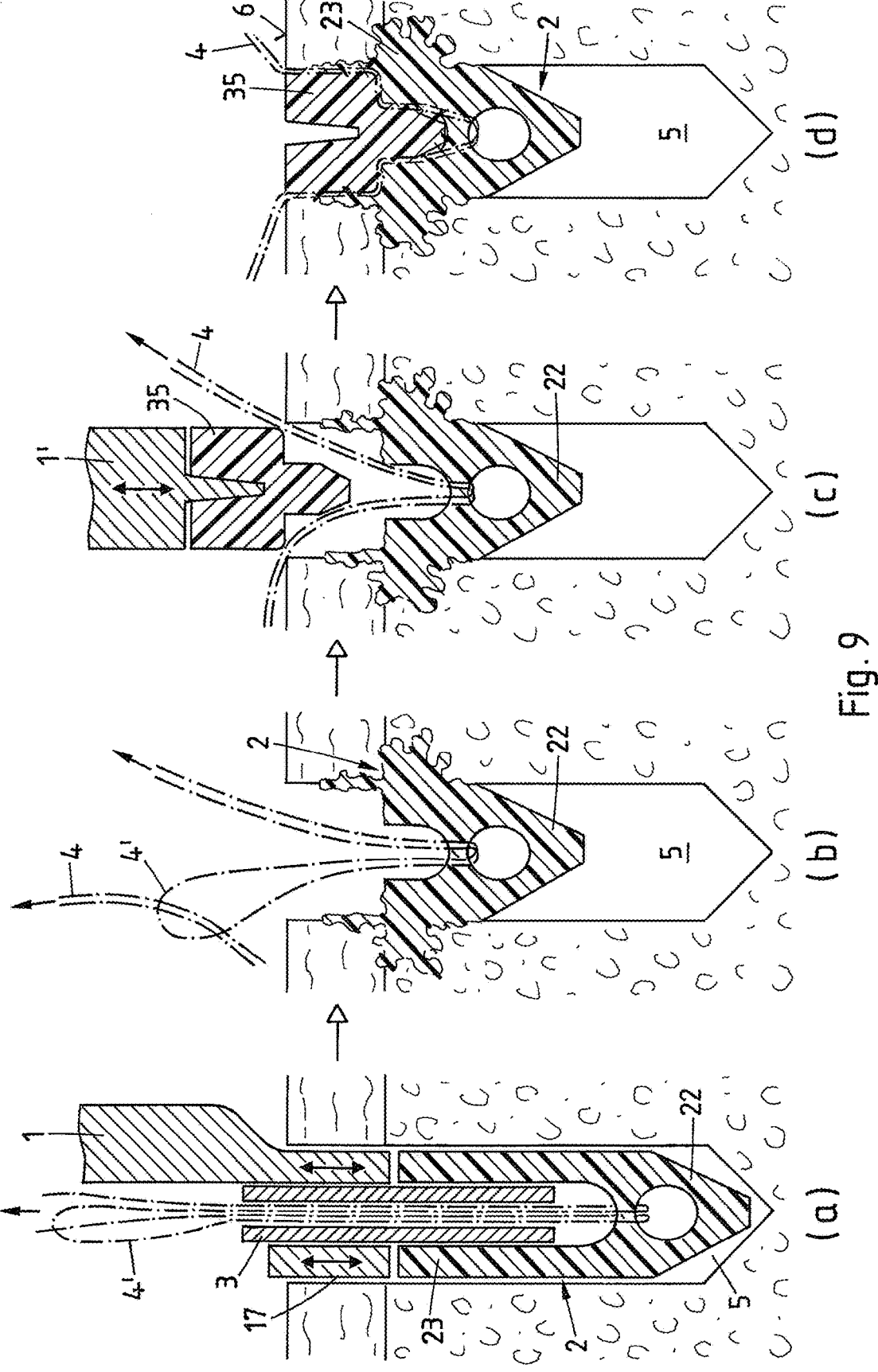
FIG. 9 illustrates a further exemplary embodiment of the method according to the invention wherein the suture is locked relative to the anchor with the aid of a locking plug.

FIGS. 8 and 9 illustrate a device and method used e.g. for fixating lateral anchors in the above briefly described double row procedure wherein the suture anchor holding the suture in a slideable manner is first fixated in the bone tissue according to the above described method, and then the suture is locked relative to the suture anchor in an additional step, thus eliminating the need for knot-tying. Of course the embodiments shown in FIGS. 8 and 9 are also applicable in other applications in which such suture locking is required.

FIG. 8 shows the same fixated anchor as FIG. 2, wherein the suture which after the fixation process carried out as illustrated in FIG. 1 is slideable relative to the anchor and is then locked in the anchor in a locking step following the fixation step, which two step procedure allows tensioning of the suture after termination of the fixation step. In the locking step, a plug 35 is forced and preferably welded into the proximal mouth of the axial channel 32 of the anchor foot 22, wherein the suture may be primarily locked by being clamped between plug 35 and anchor foot 22, or primarily by the welding procedure, or by a combination of the two. The plug 35 is positioned and secured as soon as the suture needs to be finally locked relative to the bone tissue. For being able to be welded to the anchor foot, the plug 35 and the anchor foot 22 comprise each a thermoplastic material, the two thermoplastic materials being weldable to each other preferably using ultrasonic vibration energy which is coupled into the plug 35 by application of a suitable vibration tool (not shown) to the proximal face of the plug 35. It is possible also to fix the plug 35 in the anchor foot 22 by pairing a thermoplastic plug 35 with a rough or otherwise suitably structured inner surface of channel 32 or a thermoplastic anchor foot 22 with a rough or otherwise suitably structured circumferential plug surface and by applying e.g. ultrasonic vibration energy to the plug and simultaneously forcing the plug into the channel 32. Other per se known methods for attaching the plug 35 on the anchor foot 22 and therewith locking the suture relative to the anchor foot are possible also.

FIG. 9 shows in four successive phases (a) to (d) a further exemplary embodiment of a suture fixation for which a suture anchor 2 comprising an anchor foot 22 and a thermoplastic sleeve 23 (e.g. one-piece anchor consisting of one only material having thermoplastic properties) with a loop of an auxiliary (or substitute) suture 4' threaded through its foot 22 is fixated in a hard tissue opening 5 using the device and method as e.g. described in connection with FIG. 1, wherein the auxiliary suture loop 4' takes over the suture function during the fixation according to the invention and is to be slideable relative to the fixated anchor 2. In phase (a) the anchor 2, the auxiliary suture 4', the tool 1 and the interface piece 3 are positioned for the anchoring process in a similar manner as shown on the left hand side of FIG. 1. In phase (b) the anchor 2 is shown after termination of the anchoring process and after removal of the tool 1 and the interface piece 3, in a similar manner as in FIG. 2. Phase (b) also shows the suture 4 having a surgical function (e.g. suture pair extending from medial anchors being anchored in a double row procedure) and needing locking relative to the bone tissue. Suture 4 is threaded through the loop of auxiliary suture 4' and then threaded through the anchor foot 22 by the suture loop 4' being pulled out of the anchor foot. In phase (c) the suture 4 extends through the anchor foot 22 and a locking plug 35 to be fixed (e.g. welded, preferably using ultrasonic vibration energy) to the proximal face of the anchor, i.e. to the remains of the thermoplastic sleeve 23. The locking plug 35 advantageously reaches into the axial channel of the thermoplastic sleeve 23 and is fixed in the latter also such securely locking the suture 4 relative to the anchor 2. Phase (c) also shows a locking tool 1', the locking plug 35 being attached to its distal end e.g. with the aid of a protrusion on the tool and a depression in the proximal face of the plug 35. In phase (d) the procedure is terminated, i.e. the suture 4 is securely locked relative to the anchor 2 or the bone tissue respectively. As discussed further above in connection with FIG. 8 effective locking of the suture may be effected by mechanical clamping of the suture between the plug 35 and the suture anchor 2, by the welding together of the two or by a combination of both.

As shown in FIG. 9 it is advantageous (but not necessary) to dimension anchor 2 and plug 35 such that the plug, when fixed to the anchor, is flush with the bone surface 6. For achieving an additional fixation in the bone opening it is further advantageous but not necessary to dimension the distal end portion 17 of the tool 1 such that it does not fit exactly into the bone opening 5 but such that there is a small gap between the wall of this bone opening and the distal tool end 17. During the liquefaction of the material of the thermoplastic sleeve 23, liquefied material will be pressed into this gap and, in the locking step, will be welded to the locking plug.

As already described in connection with FIG. 8 the locking plug according to FIG. 9 is preferably made of a thermoplastic material which is weldable to the remains of the thermoplastic sleeve 23 by ultrasonic welding or comprises a non-liquefiable material and a surface structure (roughness or undercut structure, e.g. thread) which is suitable for forming a positive-fit connection with the remains of the thermoplastic sleeve when forced into the latter under the influence of a pressing force and ultrasonic vibration. Of course, it is also possible to use other, per se known fixation methods for fixing the locking plug 35 to the anchor 2 such as e.g. application of an adhesive, thermal welding, a snap connection resulting in a positive-fit connection, or a thread or a combination of a plurality of such fixation methods.

The advantage of using the suture anchor and the fixation and locking method as illustrated in FIGS. 8 and 9 for establishing the lateral row of anchors in a double row procedure is that the medial and the lateral anchors can be fixated using substantially the same method and the same tools.

FIG. 10 illustrates a further additional step for the method according to the invention, the additional step serving for securing the suture 4 when tensioned from being damaged by the hard tissue edge around the mouth of the bone opening 5 and/or for securing the named edge from being damaged by the suture. The fixated anchor 2 shown in FIG. 10 is the same as the fixated anchor shown in FIG. 2. In the securing step a securing sleeve 36 is fixated to the remains of the thermoplastic sleeve 23 in substantially the same manner as described in connection with FIG. 9 for the locking plug 35, wherein the suture 4 extends loosely through the securing sleeve 36 and wherein the securing sleeve 36 is again advantageously dimensioned to be substantially flush with the bone surface 6 when fixed to the anchor 2 or to slightly protrude from the bone surface 6.

FIG. 11 is an axial section through a suture anchor 2 which comprises an anchor foot 22 and a thermoplastic sleeve 23 and which is suitable for the device and method according to the invention. The suture anchor 2 as shown in FIG. 11 is preferably a one-piece item and preferably consists of only one material having thermoplastic properties and being suitable for the in situ liquefaction constituting one feature of the method according to the invention. The anchor is preferably bio-resorbable. Such a one-piece anchor is mentioned as one exemplary anchor embodiment already further above (e.g. in connection with FIG. 9) and consists e.g. of PDLLA 70%/30% filled with up to 30% of biphasic calciumphosphate, wherein it may be advantageous to fill the material of the anchor foot 22 more than the material of the thermoplastic sleeve 23 or to strengthen the material of the anchor foot by integrating into it, as mentioned further above, a suture sleeve or a strengthening element e.g. of a polylactide of a higher cristallinity or of hydroxyapatite.

The suture anchor shown in FIG. 11 is e.g. about 15 mm long and has a circular cross section of a diameter of about 3 to 4 mm, the diameter of the axial channel of the thermoplastic sleeve 23 amounting to about 2 to 3 mm. The system of channels and/or grooves 25 corresponds approximately to the one described in connection with FIG. 1 and comprises a transversal channel 30, lateral recesses 31, an axial second channel 32 which is coaxial with the axial channel of the thermoplastic sleeve 23 and angled third channels 33 connecting the recesses 31 with the second channel 32. Therein it is possible to equip the anchor with two (or possibly more than two) parallel transversal channels 30 for accommodation of two sutures, the channels either radially or axially spaced from each other.

The invention also concerns a vibration tool (sonotrode) which is in particular suitable for the device and method according to the invention but which is applicable in other fields in which vibration energy, in particular ultrasonic vibration energy is to be used for fixating an implant to hard tissue, in particular in the field of minimally invasive surgery. The vibration tool is characterized by a rod portion and a coupling portion being attached to the proximal end of the rod portion, wherein the proximal end of the rod portion is fixed in an axial bore of the coupling portion, preferably by a press-fit connection.

FIGS. 12 to 15 show exemplary embodiments of proximal ends of vibration tools 70 showing a proximal end of the rod portion 71 being fixed in an axial bore of the coupling portion 72. FIG. 12 is a lateral view and FIGS. 13 to 15 are possible axial sections. The coupling portion 72 comprises coupling means, preferably a threaded bolt 73 designed to cooperate with a coupling means arranged on a vibration source (not shown). Such cooperating coupling means may also be designed for a bayonet coupling or similar coupling capable of transmitting mechanical vibration from the vibration source to the tool with as little energy loss as possible. The coupling portion further comprises the axial bore 74 into which the rod portion reaches and in which the rod portion is fixed, preferably by a press-fit connection or other possible fixations such as e.g. a thread or bayonet coupling, if applicable, having a screw rotation opposite the screw direction of a thread for coupling the coupling portion to the vibration source.

In comparison with a vibration tool made as one piece the vibration tool according to FIGS. 12 to 15 has several advantages: it makes rod portions of a very small cross section possible; manufacturing the two tool portions separately and then combining them is simpler than manufacturing of the tool as one piece; and rod portion and coupling portion can be made of different materials, the rod portion of a material advantageous for the vibration transfer and the coupling portion of a material advantageous for the coupling function. The rod portion is preferably a drawn wire, preferably an aluminum wire which has a limited bendability and good vibration characteristics, the coupling portion is preferably made of stainless steel, e.g. implant steel 1.4441 (X2CrNiMo 18-15-3), a coupling thread of which is less prone to get damaged in particular if the tool is to be used not only once and for each use is to be de-coupled from the vibration source. However, either rod portion or coupling portion may also be made of titanium (preferably grade 5), aluminum or stainless steel.

As illustrated in FIGS. 13 to 15, the axial bore of the coupling portion 72 in which the rod portion 71 is fixed, preferably press-fitted, may be a blind bore (FIGS. 13 and 14) or a through bore (FIG. 15) into which the rod portion is pushed to any suitable depth.

The vibration tool is preferably adapted to the vibration it is to transfer to an implant such as e.g. a suture anchor and therefore has an axial length which is approximately the same as a half of the wavelength (possibly multiplied with an integer factor) of the named vibration in the rod portion material. This half wavelength and therewith the shortest theoretical tool length is for vibration of 20 KHz frequency: 126.5 mm (titanium grade 5) and 127.5 mm (aluminum); for vibration of 25 KHz frequency: 101.2 (titanium grade 5) and 102 mm (aluminum), the numbers being applicable for coupling of the tool to the vibration source at a location of maximum vibration amplitude. Optimal tool length in particular for non-constant tool cross sections are best determined experimentally.

The above described method for fixation of a suture in hard tissue (e.g. bone tissue) concerns in particular suture anchors suitable for soft tissue attachment to hard tissue. In all the described embodiments of methods for fixating such suture anchors in hard tissue the sutures may be safeguarded against damage by heat dissipating from the material having thermoplastic properties when liquefied, by being soaked with liquid (water or saline solution) preferably before being threaded through the suture anchor or a part thereof or before being positioned in the hard tissue opening and necessarily before liquefaction of the material having thermoplastic properties.

In most parts of the above description, the suture being fixated relative to hard tissue is supposed to take over a surgical function when fixated, but also has a specific function in the fixation method, namely the function of holding the anchor or the thermoplastic sleeve respectively against the tool und moving the anchor foot against the tool when the thermoplastic sleeve gets shorter. If the method according to the invention is to be used in applications other than suture fixation or in combination with sutures which are not suitable for the named fixation functions (e.g. not easily available as shown in FIG. 9 or too weak), it is possible to carry out the method with an auxiliary suture or suture substitute, which is used instead of or in addition to the suture taking over the surgical function and which is after the fixation removed or clipped, because it has no function any more. Such suture substitute may be any flexible and elongated item such as e.g. a wire, a ribbon or a suture of suitable characteristics. In the present description, the term suture is to stand not only for sutures to take over a surgical function when fixated but also for the above described auxiliary suture or suture substitute having a function only in the method of fixating the suture anchor.

In most above described methods for fixating a suture anchor in hard tissue, a material having thermoplastic properties is liquefied to preferably penetrate hard tissue or cavities provided in the hard tissue to constitute when re-solidified a positive-fit connection between the anchor or part thereof and the hard tissue of the wall of the opening. Such positive fit connections can in all described cases be achieved also in a two-step procedure, wherein the walls of the hard tissue opening are pre-treated according to a method as described in the publications WO-2010/045751 or WO-2009/141252 (Nexilis), the disclosure of which is enclosed herein in its entirety by reference. Therein a material having thermoplastic properties is forced in a liquefied state into the hard tissue of the wall of the opening to form together with this tissue a sort of composite material substantially without coating this wall with the material having thermoplastic properties. In a second step the anchoring process being part of the method according to the invention is then carried out as described in the present description and in the cited publications, wherein the liquefied material is not able to penetrate the composite material of the wall of the opening established in the pre-treatment step, but instead is welded to the composite material of this wall. For such welding it is a condition that the material having thermoplastic properties used in the second or fixation step is weldable to the material having thermoplastic properties used in the first or pre-treatment step. Preferably the two materials having thermoplastic properties comprise the same thermoplastic polymer.

If the named pre-treatment step is carried out in a manner to form the composite material comprising the hard tissue and the material having thermoplastic material right to the mouth of the hard tissue opening, this mouth is strengthened and therewith has an enhanced capacity to resist being cut by the suture fixated in the hard tissue opening by the anchor fixated therein, when this suture is tensioned, which means that a similar effect as described in connection with FIG. 10 is achieved.

If the named pre-treatment step is carried out only in an outer region of the hard tissue (e.g. for strengthening a damaged or very thin cortical bone layer), the composite material comprising the hard tissue and the material having thermoplastic material will form a ring at the mouth of the hard tissue opening serving as a quasi cortical layer underneath which the suture anchor is then anchored as shown in FIG. 2.

What is claimed is:

1. A method for fixating a suture anchor in a hard tissue with the aid of a material having thermoplastic properties and energy transmitted to the suture anchor for in situ liquefaction of at least part of the material having thermoplastic properties, the method comprising the steps of:
    providing a hard tissue opening having a cross section slightly larger than a cross section of the suture anchor;
    providing a tool having a distal end comprising a distal tool face and an axial channel with a distal mouth located in the distal tool face;
    providing a suture and a suture anchor having an anchor foot and a thermoplastic sleeve comprising the material having thermoplastic properties wherein the anchor foot is equipped for holding a loop of the suture in a way that end sections of the suture reaching through the thermoplastic sleeve and a portion of the distal tool face;
    coupling a proximal end of the tool to an energy source;
    straightening or tensioning the suture by pulling the end sections of the suture reaching through the thermoplastic sleeve and a portion of the distal tool face in a proximal direction,
    positioning the distal tool face in the hard tissue opening;
    activating the energy source, thereby starting liquefaction of the material having thermoplastic properties;
    keeping the energy source active and moving the anchor foot relative to the tool in a proximal direction with the aid of the suture being kept straightened or tensioned, as the thermoplastic sleeve gets shorter through further liquefaction, for a time sufficient to liquefy at least part of the thermoplastic sleeve;
    de-activating the energy source and releasing the end sections of the suture reaching through the thermoplastic sleeve and a portion of the distal tool face; and
    removing the tool.

2. The method according to claim 1, further comprising a step of fixing an additional thermoplastic element to the anchor foot or to remains of the thermoplastic sleeve.

3. The method according to claim 2, wherein the additional thermoplastic element is a locking element for locking the suture.

4. The method according to claim 3, wherein the locking element is a locking plug.

5. The method according to claim 4, wherein the locking plug is welded with the aid of vibrational energy into a channel of the anchor foot or to the remains of the thermoplastic sleeve.

6. The method according to claim 2, wherein the additional thermoplastic element is a cannulated sleeve for protecting the bone proximal to the remains of the thermoplastic sleeve from the suture cutting into the bone.

7. The method according to claim 1, wherein the anchor foot comprises a system of channels and/or grooves suitable for slidably holding the loop of the suture.

8. The method according to claim 1, wherein the distal face of the thermoplastic sleeve is fixed to the anchor foot.

9. The method according to claim 1, wherein the anchor foot comprises a tube-shaped proximal protrusion reaching into the thermoplastic sleeve.

10. The method according to claim 1, wherein the tool or the suture anchor comprises a substantially tube-shaped interface piece having a distal end being couplable or coupled to the anchor foot and wherein the interface piece is designed to be able to reach through the thermoplastic sleeve and to be located in the axial channel of the distal tool end.

11. The method according to claim 10, wherein, in the step of removing, the tool is removed from the anchored suture anchor.

12. The method according to claim 11, wherein the interface piece is removed together with the tool.

13. The method according to claim 1, wherein the anchor foot is designed to allow production of a supra-cortical body during fixation process which cannot pass through the hard tissue opening.

14. The method according to claim 1, wherein, in the step of positioning, a distal face of the tool is positioned within the hard tissue opening, and wherein the distal face of the tool and/or the thermoplastic sleeve are designed for starting liquefaction at the proximal face of the thermoplastic sleeve.

15. The method according to claim 14, wherein the tool comprises energy directors at the distal tool face or the thermoplastic sleeve comprises energy directors at a proximal face suitable to provoke liquefaction of the thermoplastic sleeve at its proximal end.

16. The method according to claim 1, wherein, during the step of keeping and moving, the tension of the suture is kept constant.

17. The method according to claim 1, wherein, in the step of providing the hard tissue opening, the anchor foot is forced into the hard tissue.

18. The method according to claim 1, wherein the suture is an auxiliary suture used for fixation of the suture anchor and wherein a further suture is threaded through the anchor foot.

19. The method according to claim 1, wherein the method serves for fixation of a suture anchor beyond a hard tissue opening.

\* \* \* \* \*